US007981692B2

(12) United States Patent
Boman

(10) Patent No.: US 7,981,692 B2
(45) Date of Patent: Jul. 19, 2011

(54) IMMUNOASSAYS TO DETECT DISEASES OR DISEASE SUSCEPTIBILITY TRAITS

(75) Inventor: Bruce M. Boman, Gladwyne, PA (US)

(73) Assignee: **CA*TX Inc.**, Gladwyne, PA (US)

(*) Notice: Subject to any disclaimer, the term of this patent is extended or adjusted under 35 U.S.C. 154(b) by 0 days.

(21) Appl. No.: 12/975,270

(22) Filed: Dec. 21, 2010

(65) Prior Publication Data

US 2011/0091895 A1    Apr. 21, 2011

Related U.S. Application Data

(62) Division of application No. 11/545,660, filed on Oct. 10, 2006, now Pat. No. 7,867,717, which is a division of application No. 09/480,389, filed on Jan. 11, 2000, now Pat. No. 7,148,016.

(60) Provisional application No. 60/116,247, filed on Jan. 14, 1999.

(51) Int. Cl.
*G01N 33/53* (2006.01)
*G01N 33/48* (2006.01)
*G01N 33/566* (2006.01)
*G01N 33/567* (2006.01)

(52) U.S. Cl. ............ 436/501; 436/503; 436/63; 436/64; 436/504; 436/505; 436/518; 435/7.1; 435/7.92

(58) Field of Classification Search .................. 436/63, 436/64, 501, 503, 504, 505, 518; 435/7.1, 435/7.92
See application file for complete search history.

(56) References Cited

U.S. PATENT DOCUMENTS

| 5,591,826 | A  | 1/1997  | de la Chapelle et al. ...... 530/350 |
| 5,602,243 | A  | 2/1997  | Vogelstein .................... 536/24.3 |
| 5,650,281 | A  | 7/1997  | Vogelstein ........................ 435/6 |
| 5,709,998 | A  | 1/1998  | Kinzler et al. ..................... 435/6 |
| 5,837,443 | A  | 11/1998 | de la Chapelle et al. ......... 435/4 |
| 5,922,855 | A  | 7/1999  | Liskay et al. ................ 536/23.5 |
| 6,048,701 | A  | 4/2000  | Kinzler et al. ................. 435/7.1 |
| 6,191,268 | B1 | 2/2001  | Liskay et al. ................ 536/23.5 |
| 6,538,108 | B1 | 3/2003  | Liskay et al. ............... 530/387.1 |
| 2003/0224463 | A1 | 12/2003 | Liskay et al. ................ 435/7.23 |

FOREIGN PATENT DOCUMENTS

| EP | 0 507 852 B1 | 4/1998 |
| WO | WO 91/09964 | 7/1991 |
| WO | WO 95/14085 | 5/1995 |
| WO | WO 95/16793 | 6/1995 |

OTHER PUBLICATIONS

Boddrich et al., "Reduced Neurofibromin Content but Normal Gap Activity in a Patient with Neurofibromatosis Type 1 Caused by a Five Base Pair Duplication in Exon 12B of the NF1 Gene," *Biochemical and Biophysical Research Communictions*, 214(3): 895-904 (Sep. 25, 1995).

Boehringer-Mannheim, GmBH, "New Detection Methods for the Protein Truncation Test, Nonradioactive (PTT)," *Biochemica*, 3: 21 (1997).
Boehringer-Mannheim, "More New Products to Meet Your Changing Needs," *Biochemica*, 1: 4-5 (1997).
Boehringer-Mannheim, "Protein Truncation Test, Nonreadioactive," test kit pamphlet Cat. No. 1 888 439 (1997) accompanied by advertisement therefor.
Boman, B.M., "Biologic Functions of the Genes Responsible for Familial Cancer," *Current Opinion in Oncology*, 6: 90-95 (1994).
Boman, et al., "Radioimmunoassay of the *APC* Gene Product Using Antibodies against Its Middle and Carboxyl Regions," *Biochem. Biophys. Res. Comm.*, 206(3): 909-915 (1995).
Charbonnier et al., "Alternative Splicing of *MLH1* Messenger RNA in Human Normal Cells," *Cancer Research*, 55: 1839-1841 (May 1, 1995).
Chop et al., "Immunodetection of the Presence or Absence of Full-Length *APC* Gene Product in Human Colonic Tissues," *Anticancer Res.*, 15: 991-998 (1995).
Czech et al., "Proteolytical Processing of Mutated Human Amyloid Precursor Protein in Transgenic Mice," *Molecular Brain Research*, 47: 108-116 (1997).
Drummond et al., "Cisplatin and Adriamycin Resistance Are Associated with MutL-alpha and Mismatch Repair Deficiency in an Ovarian Tumor Cell Line," *The Journal of Biological Chemistry*, 271(33): 19645-19648 (1996).
Hemminki et al., "Loss of the Wild Type *MLH1* Gene is a Feature of Hereditary Nonpolyposis Colorectal Cancer," *Nature Genetics*, 8: 405-410 (Dec. 1994).
Hogervorst, F.B.L., "The Protein Truncation Test (PTT)," *Promega Notes Magazine*, 62: 7-14 (1997).
Froggatt et al., "Mutation Screening of MSH2 and MLH1 mRNA in Hereditary Non-Polyposis Colon Cancer Syndrome," *J. Med. Genet.*, 33: 726-730 (1996).
Kolodner and Alani, "Mismatch Repair and Cancer Susceptibility," *Current Opinion in Biotechnology*, 5: 585-594 (1994).
Levy et al., "Inactivation of Both *APC* Alleles in Human and Mouse Tumors," *Cancer Res.*, 54: 5953-5958 (Nov. 15, 1994).
Lynch and Lynch, "25 Years of HNPCC," *Anticancer Research*, 14: 1617-1624 (1994).
Lynch et al., "Hereditary Nonpolyposis Colorectal Cancer—Lynch Syndromes I and II," Gastroenterology *Clinics of North America*, 17(4): 679-712 (Dec. 1988).
Marchuck, D.A., "Genetic Abnormalities in Hereditary Hemorrhagic Telangiectasia," *Current Opinion in Hematology*, 5: 332-338 (1998).
Meyers et al. "Cell Cycle Regulation of the Human DNA Mismatch Repair Genes *hMSH2*, *hMLH1* and *hPMS2*," *Cancer Research*, 57: 206-208 (Jan. 15, 1997).

(Continued)

*Primary Examiner* — Alana M. Harris
*Assistant Examiner* — Anne L Holleran
(74) *Attorney, Agent, or Firm* — Leona L. Lauder; Joan C. Harland

(57) ABSTRACT

Disclosed are immunoassay methods for the diagnosis/prognosis of diseases and disease susceptibility traits associated with gene mutations that cause protein truncation or allelic loss. The levels of one or more targeted wild-type proteins expressed by a subject gene or genes are immunologically quantitated in biological samples. Results indicating that a targeted wild-type protein is not present in an assayed sample, or that approximately 50% of the normal amount of such a wild-type protein is present in an assayed sample are considered to be positive for a mutation in one or both alleles of a subject gene, and correlated with the disease or the disease susceptibility trait associated with that mutation or mutations. Normal cells, particularly normal peripheral blood lymphocytes, are preferred biological samples.

13 Claims, No Drawings

OTHER PUBLICATIONS

Miret et al., "Characterization of a DNA Mismatch-Binding Activity in Yeast Extracts," *The Journal of Biological Chemistry*, 268(5): 3507-3513 (1993).

Mortola and Nasto, "Brown Adipose Tissue and Its Uncoupling Protein in Chronically Hypoxic Rats," *Clinical Science*, 93: 349-354 (1997).

Pece et al, "Mutant Endoglin in Hereditary Hemorrhagic Telangiectasia Type 1 Is Transiently Expressed Intracellularly and Is Not a Dominant Negative," *J. Clin. Invest.*, 100(10): 2568-2579 (Nov. 1997).

Roest et al., "Protein Truncation Test (PTT) to Rapidly Screen the DMD Gene for Translation Terminating Mutations," *Neuromusc. Disord.*, 3(5/6): 391-394 (1993).

Smith et al., "The *APC* Gene Product in Normal and Tumor Cells," *PNAS* (USA) 90: 2846-2850 (Apr. 1993).

Powell et al., "Molecular Diagnosis of Familial Adenomatous Polyposis," *The New England Journal of Medicine*, 329(27): 982-1987 (Dec. 30, 1993).

Stankovic et al., "*ATM* Mutations and Phenotypes in Ataxia-Telangiectasia Families in the British Isles: Expression of Mutant *ATM* and the Risk of Leukemia, Lymphoma, and Breast Cancer," *Am. J. Hum. Genet.*, 62: 334-345 (1998).

Tannergard et al., "Mutation Screening in the *hMLH1* Genes in Swedish Hereditary Nonpolyposis Colon Cancer Families," *Cancer Research*, 55: 6092-6096 (Dec. 15, 1995).

Van Der Luijt et al., "Rapid Detection of Translation-Terminating Mutations at the Adenomatous Polyposis Coli (APC) Gene by Direct Protein Truncation Test," *Genomics*, 20: 1-4 (1994).

Wagner et al., "Mutation Detection Using Immobilized Mismatch Binding Protein (MutS)," *Nucleic Acids Research*, 23(19): 3944-3948 (1995).

Wei et al., "Reduced Expression of Mismatch Repair Genes Measured by Multiplex Reverse Transcription-Polymerase Chain Reaction in Human Gliomas," *Cancer Research*, 57(9): 1673-1677 (1997).

IMMUNOASSAYS TO DETECT DISEASES OR DISEASE SUSCEPTIBILITY TRAITS

This application is a divisional application of U.S. application Ser. No. 11/545,660, filed Oct. 10, 2006, now U.S. Pat. No. 7,867,717 which is a divisional application of U.S. application Ser. No. 09/480,389, filed Jan. 11, 2000, now U.S. Pat. No. 7,148,016, which claims priority from U.S. Provisional Application No. 60/116,247, filed Jan. 14, 1999. This application claims priority from all of the aforementioned U.S. patent applications and patent.

FIELD OF THE INVENTION

The invention disclosed herein is in the field of medical genetics, relating to the diagnosis and prognosis of disease and disease susceptibility, particularly in the field of oncology. More specifically, the invention concerns immunoassays that detect cellular levels of targeted full-length proteins, wherein an abnormally low level of a targeted full-length protein, or wherein the absence of such a targeted full-length protein, reflects a mutation or mutations in a subject gene. The gene mutations of interest are those associated with disease or disease susceptibility, e.g., cancer or a predisposition to cancer.

BACKGROUND OF THE INVENTION

The detection of carriers of deleterious, mutant alleles is very useful medically to guide the clinical treatment of a patient. That is, it is valuable to know whether a person has a germline or an acquired mutation associated with a disease or susceptibility to a disease.

For example, pre-operatively identifying a colon cancer patient who carries a germline mutation in a mismatch repair gene associated with hereditary non-polyposis colon cancer (HNPCC) guides a surgeon in deciding whether or not to perform a total colectomy or a partial colectomy. If the patient has a germline mutation, then the chance for a second primary colon cancer is extremely high (perhaps 70%). In that case, a total colectomy is usually recommended as the initial surgical treatment. The objectives of the surgery would be to treat the colon cancer that already exists and to prevent the development of new colonic malignancies. The presence of a germline mutation in a cancer patient will not only lead to differences in the surgical treatment of the cancer, but also to possible differences in the need for adjuvant chemotherapy after colectomy.

The ability to identify the presence of a germline mutation in patients will also lead to more effective approaches toward cancer prevention and early detection of other cancer types (e.g., besides colon cancer) that such patients are at risk to develop. In other words, the information from a test that identifies HNPCC-affected colon cancer patients should trigger a second clinical screen of those patients for extracolonic cancers which could also be life-threatening.

In addition, positive diagnoses of germline mutations in cancer patients will facilitate testing for detection of germline mutation carriers in their family members. Such testing will lead to more effective cancer prevention strategies and to better clinical management for cancers that are detected in family members. Thus, the information provided by this invention will also be useful to the physician in recommending the screening of other members of the patient's family since the finding of a germline mutation puts those individuals at high risk for colon cancer and other cancers.

A major problem in the diagnosis/prognosis of hereditary diseases is the enormous amount of work and cost involved in performing current molecular based assays to identify hereditary traits associated with a disease, such as HNPCC, or disease susceptibility. The instant invention provides more feasible methods, immunoassays, to detect such hereditary traits. The assays of this invention are relatively simple, rapid (24 hour turnaround), high throughput and inexpensive. The assays of this invention make feasible the screening of entire populations at risk for such hereditary diseases. Also, the assays of this invention can identify carriers of disease-associated hereditary traits before they develop a disease, such as cancer.

The assays of this invention are based on the assumption that gene expression directly relates to gene dosage, that is, the presence of two wild-type alleles will result in the expression of twice the amount of full-length wild-type protein than would occur if only one wild-type allele were present. In accordance with this invention, immunoassays are used to measure a reduction from normal in the amount of full-length protein expressed by a subject gene. In contrast, mutations in genes, such as mismatch repair (MMR) genes, are classically detected by DNA sequence analysis and/or in vitro translation-type assays [Giardiello, F. M., "Genetic Testing in Hereditary Colon Cancer," *JAMA*, 278: 1278-1281 (1997)], tests which are costly, time consuming and only offered in select academic and commercial reference labs.

Representative immunoassays are disclosed which are used to screen primarily for certain types of hereditary colorectal cancer (CRC) or a predisposition to hereditary CRC. Such representative immunoassay methods to screen for hereditary CRC or a predisposition thereto are based on the detection of cellular full-length protein level changes that are due to either (1) mutations of the adenomatous polyposis gene (APC), a mutation that is associated with familial adenomatous polyposis (FAP), or to (2) mutations of mismatch repair (MMR) genes, particularly, MLH1, MSH2, PMS1, PMS2, and MSH6, mutations that are associated with hereditary non-polyposis colon cancer (HNPCC).

Molecular genetic methods, such as those based on the detection of mutations in the DNA sequence of an allele of a gene of interest, have been used to diagnose individuals carrying hereditary colon cancer traits such as HNPCC and FAP. Although such tests can be highly specific and are fairly easy to perform when the precise target mutation is known, e.g., when screening HNPCC kindreds, such tests are difficult to perform, when the precise target mutation is not known. In the latter case, finding a small DNA mutation among a panel of large MMR genes becomes daunting, akin to finding a needle in a haystack. It is precisely in this situation that the immunoassays of this invention become so practical because they are rapid and relatively inexpensive.

Further, a positive finding in the immunoassay testing of this invention can be confirmed by DNA sequencing in a small fraction of the time that would have been necessary had DNA tests alone been used. Thus, the immunoassays of this invention may become useful as a complementary "pre-test". This invention may also support molecular genetic tests in the diagnosis of affected members of known kindreds in which the mutation has already been identified.

As indicated above, unknown mutations are very difficult to detect by molecular genetic tests. Unknown mutations are those found in probands, isolated cases and kindreds not yet studied. The germline mutations in such populations, which mainly involve single base pair changes, small insertions, and small deletions, may be distributed over a large portion of a gene and may involve any one of several possible loci. Moreover, the large size of the coding region makes identification of mutations by gene sequencing very difficult, labor intensive, and costly. Therefore, other techniques have been developed and are used to detect the presence of DNA variations and mutations. Such techniques include denaturation gradient gel electrophoresis (DGGE), single strand conformation polymorphism (SSCP) analysis and RNAase protection analysis. However, each of those other approaches also has drawbacks and/or limitations, particularly in sensitivity. For example, the sensitivity of those techniques for detecting APC mutations in FAP patients is only 30-70%, depending upon the method used. Newer techniques have been developed to detect mutations by analyzing translation products synthesized in vitro, but only have a slightly better sensitivity.

Most of the molecular genetic approaches discussed above are designed to detect single base pair changes, small insertions, and small deletions and/or mutations that lead to termination of translation. However, in some instances, deletion of the entire gene may occur in the germline of patients. This is yet another drawback of earlier methods because deletions of the entire gene are missed by molecular genetic approaches. Furthermore, some patients may have promoter or splicing mutations that lead to reduced levels of normal transcripts, i.e., mutations located outside the coding region that is analyzed by most molecular methods. In contrast, the immunoassay methods of this invention, by detecting the level of wild-type protein, may have greater sensitivity than the molecular genetic approaches, since they are able to detect, in addition to standard mutations, the mutations involving allelic loss, and mutations in the promoter, enhancer and splice site regions.

Another disadvantage of current molecular genetic techniques is that the technology of molecular genetics is not established in most pathology laboratories. Also, the results of molecular genetic assays often cannot be obtained quickly, for example, prior to surgery. Although molecular genetic tests can be performed on cancer tissue samples, the question whether the mutation in the cancer cells was acquired or germline would not be answered.

For example, one approach currently being explored is the detection of microsatellite instability (i.e., mutations in repetitive DNA sequences) in tumor specimens, rather than detection of specific MMR mutations [Dietmaier et al., "Diagnostic microsatellite instability: Definition and correlation with mismatch repair protein expression," Cancer Res., 57: 4749-4756 (1997)]. The microsatellite approach involves molecular biologic techniques (PCR or Southern Blot analysis) to screen for genetic changes in a panel of different genetic loci (usually 5 or more genes are simultaneously analyzed for microsatellite instability). The microsatellite approach is fairly easily performed by a molecular geneticist, and the aim is to identify which polyps have arisen from a MMR mutation. Again, however, this approach does not distinguish between acquired and germline MMR mutations and provides no information that identifies which of the five known MMR genes is mutant.

The instant immunoassay methods, in contrast, can be done in any pathology laboratory and can be developed to be cost-effective to screen large numbers of individuals in a short amount of time. The assays can be performed quickly, and the results are immediately obtainable. Once the change in the product of a particular gene is identified by the immunoassay methods of the invention, molecular genetic tests can then be employed to determine the precise location of the mutation.

SUMMARY OF THE INVENTION

Immunoassay methods of this invention can be adapted to detect disease or disease susceptibility traits in plants, viruses, animals, fungi, and members of the kingdoms Prokaryotae and Protoctista, such as bacteria and protozoans. Preferably the immunoassay methods of this invention are used to detect disease or disease susceptibility in vertebrates, more preferably in mammals, and still more preferably in humans.

The immunoassay methods of this invention are based on the theory that normal individuals, that is, those without a mutation in a subject gene, will have 100% expression of that subject wild-type gene product and also 100% expression of a wild-type reference gene product. In contrast, an individual with a mutation in an allele of that same gene will in theory have only 50% expression of the subject wild-type gene product, while maintaining 100% expression of the reference wild-type gene product.

In one preferred aspect, the immunoassay methods of this invention detect disease or disease susceptibility associated with a germline mutation in one or both alleles of a subject gene. The immunoassay methods of this invention are also in this aspect premised on the assumption that germline mutations in two different genes of one individual are very rare.

Representative immunoassays of this invention are those to detect susceptibility to HNPCC and FAP in humans. In the case of screening for the HNPCC susceptibility trait, the amounts of MLH1 and MSH2 wild-type proteins (the expression products of the two major MMR genes) are measured from a sample from an individual, e.g. from freshly prepared lymphocytes. Almost all individuals with a germline MMR mutation will have 100% of one of those two full-length MMR proteins but only 50% of the other full-length protein.

After applying these methods to (a) a normal population and (b) to a population of verified HNPCC cases, the immunoassay methods of this invention allow for the setting of criteria that enable one to distinguish between normal and abnormal levels of expression of full-length MMR proteins. The methods rely on the ratio of the expression level of the subject wild-type gene product of interest and that of a reference gene product, and the calculation of a ratio of one to the other. For example, in the case of MMR mutations, the ratio of the amount of MSH2 protein to the amount of MLH1 protein can be used. It is then determined whether the numerical value of the ratio falls clearly in a normal range or clearly in a range predicted for 50% loss of expression of the subject gene product, e.g., 50% loss of expression of either MSH2 or MLH1 protein when screening for HNPCC.

Another recommended target population for the immunoassay methods of this invention are patients identified as having CRC (10% of CRC patients are predicted to carry MMR mutations). If a CRC patient is found to be a carrier of an MMR mutation, it would be advisable to encourage blood relatives of the patient (e.g., the proband) to undergo screening for polyps and/or CRC-related cancers because those relatives have now been identified as being at higher risk for CRC. (A proband is the first member of a family to be conclusively identified as having a genetic trait, such as the HNPCC trait.)

In one aspect, the immunoassays of this invention are designed to identify carriers of hereditary traits associated with disease, such as the hereditary HNPCC and FAP traits. The read-out of the assay, i.e. the levels of wild-type protein, correlate with genotype. In this way, the assays distinguish between cells that are homozygous and those that are heterozygous for a wild-type allele, and thus distinguish between individuals with and without a hereditary trait. This invention addresses one of the problems of inadequate management of CRC by providing improved and earlier diagnosis of the most common form of hereditary colon cancer, HNPCC, a disorder which accounts for about 10% of patients that have been diagnosed with CRC.

The immunoassays of this invention may be adapted to measure full-length (wild-type) proteins associated with many other hereditary and genetic disorders (cancer and non-cancer) that are due to mutations that cause protein truncation (germline and acquired) or cause the absence of allelic protein expression. Representative genes subject to truncation-causing mutations and/or allelic loss, and the disease(s) associated with mutations in such genes are listed as follows:

| | |
|---|---|
| APC | CRC and GI cancers |
| ATM | ataxia-telangiectasia; hemangioblastoma; renal cell carcinoma; pheochromocytoma |
| BRCA1 | breast cancer |
| BRCA2 | breast cancer |
| CFTR | cystic fibrosis |
| c-myb | hematologic malignancies |
| dystrophin | Duchenne muscular dystrophy (DMD) |
| E-cadherin (HSECAD) | breast cancer and colon cancer |
| EMD | Emery-Dreifuss muscular dystrophy |
| FAA | Fanconi anemia |
| IDS | Hunter syndrome |
| MLH1 | CRC, GI, GU and GYN cancers |
| MSH2 | CRC, GI, GU and GYN cancers |
| NF1 | neurofibromatosis type 1 |
| NF2 | neurofibromatosis type 2 |
| p16 (CDKN2A and MTS1) | familial melanoma |
| PKD1 and PKD2 | polycystic kidney disease |
| PTCH | nevoid basal cell carcinoma |
| VHL | von Hippel-Lindau disease. |

Herein are described representative assays to detect mutations in the APC gene and in MMR genes. However, ones of skill in the art can readily adapt such assays to detect analogous mutations in other genes, as listed above, wherein such mutations are known to be associated with a disease or disease susceptibility (see "Immunoassays For Other Full-length Proteins", below).

In one sense, the methods of this invention can be used to screen for an abnormally low level of a targeted wild-type protein or the absence of a targeted wild-type protein in a biological sample. The level of said targeted wild-type protein can be determined by calculating the ratio of the amount of said wild-type protein to the amount of a reference protein in a biological sample, and determining whether that ratio is normal or abnormal compared to analogous normal ratios calculated in population studies of unaffected individuals. The reference protein can be unrelated to the disease or disease susceptibility trait to which the assay is directed, or can be the expression product of another subject gene that could also be associated with the disease or disease susceptibility to which the assay is directed. In that latter embodiment, the assay could be characterized as a form of differential diagnosis/prognosis, determining in one assay which of several genes is affected by a disease-associated mutation. Exemplary thereof is the assay method specifically described herein, wherein MLH1 and MSH2 are the subject genes, and susceptibility to HNPCC is the trait to which the assay is directed.

In one preferred embodiment, the immunoassay methods of this invention are designed to detect disease or a disease susceptibility trait in an organism, wherein said disease or said disease susceptibility trait is associated with a mutation or mutations in a subject gene, comprising:

(a) isolating a biological sample from said subject organism;

(b) immunologically quantitating the amount of wild-type protein expressed by said subject gene in said sample, and the amount of a reference protein expressed by a second gene in said sample;

(c) calculating the ratio of the amount of the wild-type protein expressed by said subject gene in said sample to the amount of the reference protein expressed by said second gene in said sample;

(d) determining whether or not any wild-type protein expressed by said subject gene is present in said sample, or whether or not said calculated ratio reflects an abnormally low level of said wild-type protein expressed by said subject gene in said sample; and (e) concluding that if no wild-type protein is present in said sample, that said subject gene contains a mutation in each of its alleles, or, that if the ratio calculated in step (c) indicates that there is an abnormally low level of wild-type protein in said sample, that said subject gene contains a mutation in one of its alleles, and that if either is the case, that the subject organism is affected by the disease or the disease susceptibility trait associated with said mutation or mutations. A preferred exemplary reference protein in such an embodiment is actin, tubulin, or glyceraldehyde-3-phosphate dehydrogenase.

Step (d) of that embodiment of the immunoassay methods of this invention can comprise comparing the ratio calculated in step (c) to a mean of ratios of amounts of said wild-type protein expressed from said subject gene to amounts of said reference protein in comparable biological samples from organisms of the same taxonomic classification as the subject organism, that are unaffected by said disease or by said disease susceptibility trait.

As indicated above, the expected reduction in the cellular levels of full-length protein in the case of a truncation-causing mutation or a mutation causing allelic loss would be a 50% reduction in the amount of full-length protein expressed by a subject gene. If both alleles are affected by such a mutation, one would expect a 100% reduction from normal in expression of said full-length protein. However, due to biological variability, a reduction in full-length protein expression from normal (for a single allelic mutation) could be considered herein to be a positive result, according to a threshold level that is statistically determined from the range of normal values in disease-free individuals from the general population. If the remaining allele of a subject gene becomes mutant as well, as often happens in the case of cancer, the expected read-out of the invention drops from 50% to 0%. Variability from those theoretical baselines for positive results could be ±20%, preferably ±15%, more preferably ±10%.

In another preferred embodiment, the immunoassay methods of this invention can detect a disease or a disease susceptibility trait in an organism, wherein said disease or said disease susceptibility trait is associated with a mutation or mutations in one of two or more subject genes, comprising:

(a) isolating a biological sample from said organism;

(b) immunologically quantitating the amount of wild-type protein in said sample, that is expressed by each of the subject genes;

(c) calculating the ratio of the amount of the wild-type protein expressed by one of said subject genes in said sample, to the amount of wild-type protein expressed by the other subject gene in said sample, or to each of the amounts of wild-type protein expressed by each of the other subject genes in said sample;

(d) determining whether a wild-type protein expressed by either of the subject genes, or by any of the subject genes is absent from said sample, or whether the ratio or ratios calculated in step (c) reflects or reflect an abnormally low level of a wild-type protein expressed by either of the subject genes, or by any of the subject genes in said sample; and (e) concluding that if a wild-type protein known to be normally expressed by one of the subject genes is not present in said sample, that that subject gene contains a mutation in each of its alleles, or that if the ratio or ratios calculated in step (c) indicates or indicate that there is an abnormally low level of a wild-type protein expressed by one of the subject genes in said sample, concluding that that subject gene contains a mutation in one of its alleles; and, in either case, determining that the subject organism is affected by the disease or the disease susceptibility trait associated with said mutation or mutations.

Step (d) of that embodiment may comprise comparing the ratio or ratios calculated in step (c) to the comparable mean or means of ratios calculated from the amounts of wild-type proteins expressed by the subject genes in comparable biological samples from organisms of the same taxonomic classification as the subject organism, that are unaffected by said disease or by said disease susceptibility trait.

In another aspect, this invention concerns immunoassay methods to detect a disease or a disease susceptibility trait in an organism, wherein said disease or said disease susceptibility trait is associated with a mutation or mutations in a subject gene, comprising:

(a) isolating a sample of normal cells from said organism;

(b) immunologically quantitating the amount of wild-type protein expressed by the subject gene in said sample;

(c) determining whether any wild-type protein is present in said sample, and if so, whether the amount of wild-type protein present in said sample is abnormally low in comparison to the amount of wild-type protein expressed by the subject gene in a control sample; and (d) if said wild-type protein is not present in said sample, concluding that the subject gene has a mutation in each of its alleles; or if the amount of said wild-type protein in said sample is determined to be abnormally low in comparison to the amount of wild-type protein in the control sample, concluding that the subject gene has a mutation in one allele; and in either case, correlating the conclusion with the subject organism having the disease or the disease susceptibility trait associated with said mutation or said mutations. Said normal cells are preferably normal peripheral blood lymphocytes. When the assay results indicate that the subject gene has a mutation in one allele, the abnormally low amount of wild-type protein is generally about 50% of the control amount, with the above-noted variability being operative.

The mutations associated with disease or disease susceptibility traits detected by the immunoassay methods of this invention may be germline or somatic, preferably germline. Such mutations are either truncation-causing mutations or those that cause allelic loss. Exemplary mutations are selected from the group consisting of nonsense mutations, frameshift mutations, promoter mutations, enhancer mutations, splice site mutations, null mutations, and poly-A tail mutations.

The organisms from where the biological samples are isolated may be viruses, plants, fungi, animals, or from members of the kingdoms Prokaryotae and Protoctista. Preferably, said organisms are vertebrates, more preferably mammals, and still more preferably humans.

The biological samples tested by the immunoassay methods of this invention include tissue specimens, body fluids (e.g., blood, serum, plasma), tissue extracts, cells, cell lysates, cell extracts, supernatants from normal cell lysates, supernatants from preneoplastic cell lysates, and supernatants from neoplastic cell lysates.

Preferred biological samples are cell samples, cell extracts, cell lysates, supernatants from cell lysates, tissue samples and tissue extracts. Further preferred are normal cell samples, normal cell extracts, lysates of normal cells, and supernatants of normal cell lysates. Particularly preferred are samples of peripheral blood lymphocytes (PBLs), lysates of PBLs, supernatants from lysates of PBLs, and extracts of PBLs.

Exemplary samples of body fluids can include among other fluids: blood, serum, plasma, semen, breast exudate, gastric secretions, fecal suspensions, bile, saliva, tears, sputum, mucous, urine, lymph, cytosols, ascites, pleural effusions, amniotic fluid, bladder washes, bronchoalveolar lavages, and cerebrospinal fluid. When a body fluid is the biological sample tested by a method of this invention, it is preferred that the one or more targeted full-length, wild-type gene product(s) and, if relevant, the reference protein be concentrated from a larger volume of body fluid before being quantitated by immunological means, such as, e.g. by Western blot, flow cytometry, or sandwich immunoassay.

The methods of this invention are adaptable for automation. The above-outlined assays can be embodied in automated formats. Preferred automated immunoassay systems to which the methods of this invention can be adapted are those using chemiluminescence and magnetic separation.

Abbreviations

The following abbreviations are used herein:

| | |
|---|---|
| AFAP | attenuate familial adenomatous polyposis |
| APC | adenomatous polyposis coli |
| ATCC | American Type Culture Collection |
| ATM | ataxia-telangiectasia |
| BL | bioluminescent |
| CL | chemiluminescent |
| CRC | colorectal cancer |
| DGGE | denaturing gradient gel electrophoresis |
| DMEM | Dulbecco modified Eagle medium |
| DTT | dithiothreitol |
| EDTA | ethylenediamine tetraacetic acid |
| EGTA | [ethylenebis(oxyethylenenitrilo)] tetraacetic acid |
| EIA | enzyme immunoassay |
| ELISA | enzyme-linked immunosorbent assay |
| FAP | familial adenomatous polyposis |
| FBS | fetal bovine serum |
| FITC | fluorescein isothiocyanate |
| GAPDH | glyceraldehyde-3-phosphate dehydrogenase |
| GI | gastrointestinal |
| GU | genitourinary |
| GYN | gynecologic |
| HNPCC | hereditary non-polyposis colon cancer |
| kDa | kilodalton |
| MAb | monoclonal antibody |
| MCR | mutation cluster region |
| MMR | mismatch repair |
| MW | molecular weight |
| PBL | peripheral blood lymphocyte |
| PBS | phosphate-buffered saline |
| PCR | polymerase chain reaction |
| PE | phycoerythrin |
| PMP | paramagnetic particle |
| PMSF | phenylmethylsulfonyl fluoride |
| PPV | positive predictive value |
| PTT | protein truncation test |
| Rb | retinoblastoma |
| RBC | red blood cell |
| RIA | radioimmunoassay |
| RIPA | radioimmunoprecipitation assay |
| RT | room temperature |

| | |
|---|---|
| SDS | sodium dodecyl sulfate |
| SDS-PAGE | sodium dodecyl sulfate - polyacrylamide gel electrophoresis |
| SSCP | single strand conformation polymorphism analysis |
| TGFBR2 | transforming growth factor, beta receptor 2 |
| WBC | white blood cell |
| w/v | weight to volume |

DETAILED DESCRIPTION

The assays of this invention are highly sensitive, specific, easy, rapid (24 hour turnaround), inexpensive and adaptable to automated technologies. This invention provides assays that are diagnostic/prognostic for hereditary diseases associated with a mutation of a subject gene that ultimately results in a decrease in the cellular level of wild-type product of that gene. The immunoassay methods assay for full-length proteins encoded by genes of interest. Exemplary are the immunoassays of the invention used to detect alterations in the cellular level of the protein products(s) of the APC gene associated with FAP, and of the MMR genes associated with HNPCC.

Individuals carrying a hereditary mutation associated with a trait, are considered to have a reduced gene dosage of the wild-type allele for that predisposing trait. The examples set forth below show that the assays of this invention can detect variations in gene product expression that correlate with gene dosage. The experiments described herein establish the ability of immunoassays, such as a Western blot analysis, to detect and quantitate cellular expression levels of target gene proteins, such as MMR and APC proteins, and to show that such a level correlates with the wild-type gene dosage of the subject gene.

The term "gene" is herein defined to mean a nucleotide sequence that contains a complete coding sequence for a protein product. In general, a "gene" is considered to include nucleotide sequences found upstream (e.g., promoter sequences, enhancers, etc.) or downstream (e.g., transcription termination signals, polyadenylation sites, etc.) of the coding sequences that affect the expression of the encoded protein. The term "allele" is a shorthand form of allelomorph, one of a series of possible alternative forms of a given gene differing in DNA sequence and affecting the function of a single product (RNA and/or protein).

The assays of this invention are diagnostic and/or prognostic (predictive), i.e., diagnostic/prognostic. The term "diagnostic/prognostic" is herein defined to encompass the following processes either individually or cumulatively depending upon the clinical context: determining the predisposition to a disease, determining the nature of a disease, distinguishing one disease from another, forecasting as to the probable outcome of a disease state, determining the prospect as to recovery from a disease as indicated by the nature and symptoms of a case, monitoring the disease status of a patient, monitoring a patient for recurrence of disease, and/or determining the preferred therapeutic regimen for a patient. The diagnostic/prognostic methods of this invention are useful, for example, for screening populations for the presence of neoplastic or pre-neoplastic disease, determining the risk of developing neoplastic disease, diagnosing the presence of neoplastic and/or pre-neoplastic disease, monitoring the disease status of patients with neoplastic disease, and/or determining the prognosis for the course of neoplastic disease.

Any conventional immunoassay format can be adapted to detect and quantitate (at least semi-quantitatively) the target gene protein or proteins, or the target gene protein and one or more reference proteins in accordance with this invention. Such formats include Western blots, preferably of immunoprecipitated protein, ELISAs, RIAs, competitive EIAs and dual antibody sandwich assays, among other assays commonly used in the diagnostic industry. Western blots of immunoprecipitated proteins and sandwich immunoassays are preferred, and sandwich immunoassays are particularly preferred.

Particularly preferred sandwich immunoassays are those that are either fluorescent-tagged, enzyme-linked or chemiluminescent-linked. Automated immunoassays as described herein are also preferred.

Representative of one type of ELISA test is a format wherein a microtiter plate is coated with antibodies made to a full-length protein expressed by a subject gene, or to the amino or carboxyl terminus thereof. To that is added a patient sample, for example, a tissue or cell extract or cell lysate. After a period of incubation permitting protein to bind to the antibodies, the plate is washed and another set of relevant antibodies that are labeled, e.g., linked to an enzyme, is added, incubated to allow reaction to take place, and the plate is then rewashed. Thereafter, for example, enzyme substrate is added to the microtiter plate and incubated for a period of time to allow the enzyme to work on the substrate, and the absorbance of the final preparation is measured. The change in absorbance is proportional to the quantity of subject full-length protein in the sample.

An exemplary immunoassay method of this invention to detect and quantitate a wild-type target gene product and a reference protein in a vertebrate sample comprises the steps of:

a) incubating said vertebrate sample with two sets of antibodies, one set of which binds to the wild-type target gene product, and the other set of which binds to the reference protein, wherein each set of antibodies is labeled or otherwise detectable differently from the other set;

b) examining the incubated sample to determine the amount of immune complexes comprising the wild-type target gene product and the amount of immune complexes comprising the reference protein, and calculating the ratio of those two amounts.

Another exemplary immunoassay method according to this invention is that wherein a competition immunoassay is used to detect and quantitate a wild-type target gene product and a reference protein in a vertebrate sample to determine whether there is a mutation in the target gene, comprising the steps of:

a) incubating a vertebrate sample with two sets of antibodies, each set being specific respectively to a wild-type target gene product or to a reference protein, and a certain amount of a labeled (including other visualizing means) wild-type target gene product and a certain amount of a labeled reference protein, wherein said labeled gene product and labeled reference protein are differently labeled and compete for binding to said respective antibodies with wild-type target gene product and reference protein that are present in the sample;

b) examining the incubated sample to determine the amount of labeled wild-type gene product or reference protein bound to said antibodies; and c) determining from the results of the examination in step b) the amount of target gene product and reference protein present in said sample, calculating the ratio thereof and determining, if there is a reduced amount of the target full-length protein in said sample, that there is a mutation in the target gene.

Once antibodies (including biologically active antibody fragments) having suitable specificity have been prepared, a wide variety of immunological assay methods are available for determining the formation of specific antibody-antigen complexes. Numerous competitive and non-competitive protein binding assays have been described in the scientific and patent literature, and a large number of such assays are commercially available. Exemplary immunoassays which are suitable for detecting antigen include those described in U.S.

Pat. Nos. 5,686,258; 5,695,928; 5,770,457; 3,984,533; 3,996,345; 4,034,074; and 4,098,876.

Antibodies employed in assays may be labeled or unlabeled. Unlabeled antibodies may be employed in agglutination; labeled antibodies may be employed in a wide variety of assays, employing a wide variety of labels.

Suitable detection means include the use of labels such as radionuclides, enzymes, coenzymes, fluorescers, chemiluminescers, chromogens, enzyme substrates or co-factors, enzyme inhibitors, free radicals, particles, dyes and the like. Such labeled reagents may be used in a variety of well known assays, such as radioimmunoassays, enzyme immunoassays, e.g., ELISA, fluorescent immunoassays, and the like. See for example, U.S. Pat. Nos. 3,766,162; 3,791,932; 3,817,837; and 4,233,402.

Immunoassay Test Kits

The above-outlined assays can be embodied in test kits to detect and quantitate a wild-type target gene product or products, or a target gene product and a reference protein. Such kits to detect and quantitate relevant wild-type gene products and/or reference protein(s) can comprise the gene product(s) or reference protein(s) of interest and antibodies, polyclonal and/or monoclonal specific to such wild-type gene product(s) or reference protein(s). Such diagnostic/prognostic test kits can comprise one or more sets of antibodies, polyclonal and/or monoclonal, for a sandwich format wherein said antibodies recognize epitopes on the full-length protein(s), and one set is appropriately labeled or is otherwise detectable for each gene product or reference protein of interest.

A kit for use in an enzyme-immunoassay typically includes an enzyme-linked antibody and a substrate for the enzyme. The enzyme can, for example, be linked to either an antibody specific to a protein of interest or to an antibody to such a specific antibody.

Assays for Colorectal Cancer

Improved and earlier diagnosis of colorectal cancer (CRC) is needed. There are very approximately 140,000 new cases of colon cancer diagnosed in the USA each year, and more in other countries of the world. A substantial number of those cases (about 10%) will have one of the hereditary types of colon cancer such as hereditary nonpolyposis colon cancer (HNPCC) or familial adenomatous polyposis (FAP). Diagnosis of those hereditary forms of colon cancer would, in many cases, suggest to the physician that more extensive surgery be done, and/or that indication for surgical adjuvant chemotherapy may be different, and/or that members of the patient's family should be screened. To date, however, the inventor is not aware of any practical test to identify those individuals with hereditary forms of colon cancer. Thus, development of a test for hereditary colon cancer that is simple, widely available, rapid and inexpensive should be clinically valuable to physicians.

Highlighting the value of early diagnosis of premalignant colonic lesions is a recent study which showed that a substantial and significant reduction in morbidity and mortality can be achieved by identifying HNPCC in an individual and in families and then doing rigorous clinical follow-ups (e.g., regular colonoscopic exams for adenomatous polyps). [Jarvinen, H. J., Mecklin, J. P., Sistonen, P. "*Screening reduces colorectal cancer rate in families with hereditary nonpolyposis colorectal cancer,*" *Gasterontology,* 108: 1405-1411 (1995)].

Frequency

The frequency of germline mutations involving a mismatch repair gene (responsible for HNPCC) is about 1 in every 200 to 300 individuals in any Western population. Because there is at least 90% penetrance associated with germline MMR mutations (i.e. HNPCC patients), almost all carriers will develop cancer during their lifetimes. Since, in the Western world there are over 1 billion people (U.S. and Europe), over 5 million are predicted to have a germline MMR mutation. It is important to identify such MMR mutations before the carriers develop cancer.

Of the more than 1 billion people living in the Western world, about 50% (1 in 2) will develop colorectal adenomatous polyps (hereinafter referred to simply as "polyps") by age 70. [Ransohoff and Lang, *N. Engl. J. Med.*, 325: 37 (1991).] The lifetime likelihood of developing CRC in the Western world is about 10-fold smaller or 1 in 20.

The American Cancer Society recommends that all individuals over 50 be screened for polyps. The goals of such screening are (1) early detection of CRC at a treatable stage (generally surgery); and (2) cancer prevention by identification and removal of polyps before they progress to cancer.

About 10% of all CRC cases are estimated to be hereditary cancers. Of those, only a small fraction are due to a germline mutation in the APC gene. Most hereditary colon cancer is associated with germline MMR mutations. Adenomas are known to progress to carcinomas more rapidly in patients with MMR mutations than in patients who develop sporadic, non-hereditary forms of CRC. If the outcome of a flexible sigmoidoscopy procedure (the initial clinical screen for polyps or CRC) is positive, then a gastroenterologist would typically follow up with an examination of the entire colon (a full colonoscopy) for detection of additional polyps or colorectal tumors. At this point, it is advised that a gastroenterologist employ the immunoassays of this invention to detect MMR mutations.

MMR Immunoassays

The immunoassay methods of this invention to detect mutations associated with HNPCC are based on two assumptions concerning MMR mutations: (1) that HNPCC carriers have a single germline mutation in one of the following four DNA mismatch repair (MMR) genes—hMLH1, hMSH2, hPMS2 and hPMS1; and (2) that such a mutation leads to a reduced cellular level of the full-length wild-type protein that is coded for by the gene (gene product being theoretically considered proportional to gene dosage). If one of the two alleles of an MMR gene is mutant, it is assumed in accordance with this invention that there is a 50% reduction in the amount of full-length protein synthesized in such an individual's body tissues. Such an immunoassay method would be especially useful after positive findings of polyps during endoscopy.

Schemes 1 and 2 below illustrate clinical uses of assays to detect mutations in the MMR genes—MSH2 and MLH1.

SCHEME 1. Target Population: Colon and Other Types of Cancer Patients

INITIAL DIAGNOSIS OF DIGESTIVE TRACT, ENDOMETRIAL OR OVARIAN CANCER

Perform Venopuncture (5-10 ml blood) Before Surgery

Immunoassay for MSH2 & MLH1 Protein Levels in Peripheral WBCs

Reduced Level        Normal Level

        

-continued

1) Alter Surgical Treatment (e.g. Subtotal Colectomy in a Colon Cancer Patient or Bilateral Ophorectomy & Hysterectomy in a Gynecological Ovarian Cancer Patient) — Conventional Surgical Treatment

⇓

2) Clinically Evaluate the Patient for Cancers at Other Sites & Institute Cancer Screening.

⇓

3) Test other Family Members for Carrier Status & If Positive Institute Proper Clinical Evaluation, Routine Screening, & Management Measures.

SCHEME 2. Target Population: Patients with Premalignant Colonic Lesions

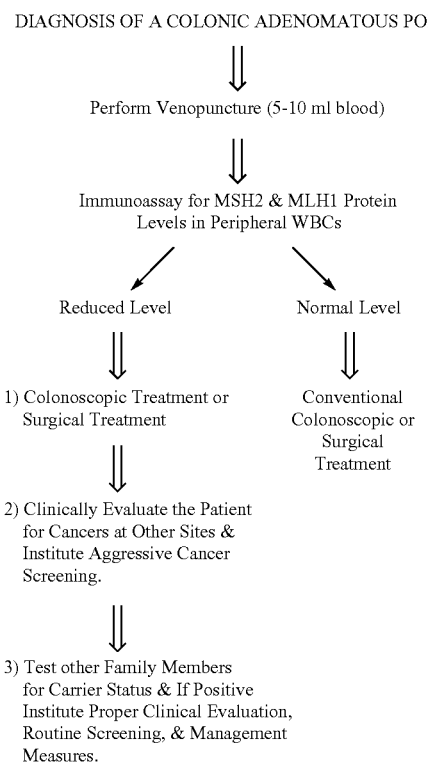

DIAGNOSIS OF A COLONIC ADENOMATOUS POLYP

⇓

Perform Venopuncture (5-10 ml blood)

⇓

Immunoassay for MSH2 & MLH1 Protein Levels in Peripheral WBCs

Reduced Level / Normal Level

1) Colonoscopic Treatment or Surgical Treatment — Conventional Colonoscopic or Surgical Treatment

⇓

2) Clinically Evaluate the Patient for Cancers at Other Sites & Institute Aggressive Cancer Screening.

⇓

3) Test other Family Members for Carrier Status & If Positive Institute Proper Clinical Evaluation, Routine Screening, & Management Measures.

The examples below illustrate the immunoassay methods used to develop this invention to detect MMR mutations associated with HNPCC and other cancers. The focus on the HNPCC assays of this invention is primarily on two of the MMR genes (MLH1 and MSH2), because mutations in those two genes have been shown to account for the majority (~90%) of identifiable mutations in HNPCC cases. [Peltomäki and de la Chapelle, "Mutations Predisposing to Hereditary Nonpolyposis Colorectal Cancer," *Adv. Cancer Rev.*, 71: 93-119 (1997)]. Many of the known mutations in MMR proteins result in truncated proteins. [Id.]

Patients having a mismatch repair genetic defect in their germline are not only predisposed to develop colon cancer, but are also at a significantly higher risk to develop endometrial, ovarian, prostate, stomach, small intestine, pancreas, and biliary tract cancers as well. Based on the penetrance rate and the frequency of isolated cases, it is estimated that over 40% of patients with germline mismatch repair mutations will develop cancer and not have a family history of cancer (over 400,000 hereditary cancer cases will have a negative family history).

A potential limitation of the assays of this invention are that they do not detect mutations, such as, missense mutations, that result in a full-length gene product. An estimate of that limitation for MMR mutations can be determined from the following information [Peltomäki and de la Chapelle, supra]: (1) the proportion of HNPCC cases attributable to different mutations—MSH2 and MLH1 account for 90%; the rest (MSH6; PMS2; PMS1; TGFBR2) account for the remaining 10%; (2) the relative proportions of truncating and non-truncating mutations in MSH2 and MLH1 genes are—MSH2 [non-truncating (missense)=7% & truncating (frameshift, nonsense & in-frame deletion)=93%], and MLH1 [non-truncating (missense)=31% & truncating (frameshift, nonsense & in-frame deletion)=69%]. Based on that information, the proportion of all MMR mutations that an assay of this invention could successfully detect using anti-MLH1 and anti-MSH2 is predicted to be at least 70%.

The inability to detect about 30% of HNPCC cases is about the same magnitude as reported for other molecular genetic tests. [Peltomäki and de la Chapelle, supra; Giardiello, F. M., supra]. However, the proportion of hemizygote cases that involve non-truncating mutations may be an overestimate, because other mutations, such as, allelic loss, and promoter mutations (not readily detected by other molecular genetic tests), should be detected by the assays of this invention, if such mutations, e.g., those involving allelic loss or promoter regions, eliminate or reduce expression from one allele of a MMR gene. Moreover, immunoassays of this invention to detect full-length PMS1 and PMS2 protein in conjunction with the MLH1 and MSH2 assay would significantly reduce the numbers of MMR mutations not identified.

Further, in non-truncating missense mutations that involve substitution of an amino acid, a change which should not alter the overall length of the polypeptide backbone of the protein, different approaches can be used to detect those mutations if immunoassay is used for diagnosis. For example, an important potential consequence of an amino acid substitution (in regard to the ability to detect them) is that such a substitution may alter the three dimensional native protein structure to a sufficient extent that it changes the epitope exposure in native MMR proteins, and this may be detectable by immunoassay using antibodies to specific epitopes.

Thus, the flow cytometric immunoassay may be capable of detecting some types of protein alterations due to missense mutations since flow cytometry involves analysis of permeabilized cells, a situation in which the 3-D native MSH2 and MLH1 protein structures should be preserved. Such mutations could be detected by alternative strategies because assays for MMR mutations are being developed in other laboratories which are based on detecting functional changes in enzymatic activity for cellular mismatch repair [Bennett et al., *Cancer Res.*, 57: 2956 (1997)]. Another possibility includes detecting changes in protein mobility using 2-D gel electrophoresis systems or high performance liquid chromatography (HPLC) analogous to assays for diagnosing hemoglobinopathies [ESA, Inc.; Chelmsford, Mass. (USA)].

Antibodies to MMR Proteins

Anti-human MLH1, anti-human MSH2 and anti-mouse PMS2 are commercially available from PharMingen (San Diego, Calif.). Anti-human MLH1 and anti-human MSH2 are also commercially available from Oncogene Research Products (Cambridge, Mass.). Table 1 characterizes those commercially available antibodies.

TABLE 1

Commercially Available Antibodies Against Mismatch Repair Proteins

| Target Protein | Epitope | Type/Isotype | Immuno-precipitation | Western Blot Assay | Immuno-histo-chemistry | Source |
|---|---|---|---|---|---|---|
| anti-hMSH-2 | unknown | monoclonal mouse IgG1 | NT | + | + | PharMingen |
| anti-hMSH2 | carboxy terminus | monoclonal mouse | + | + | + | Oncogene |
| anti-MSH2 | amino terminus | monoclonal mouse | + | + | + | Oncogene |
| anti-MSH2 | full-length protein | polyclonal rabbit | + | + | + | Oncogene |
| anti-hMLH1 | unknown | monoclonal mouse IgG1 | + | NT | + | Oncogene |
| anti-hMLH1 | unknown | polyclonal rabbit | − | + | − | Oncogene |
| anti-hMLH1 | unknown* | monoclonal mouse IgG1 | + | NT | + | PharMingen |
| anti-hMLH1 | unknown | monoclonal mouse | − | + | + | PharMingen |
| anti-mouse PMS2 | unknown | polyclonal rabbit | NT | + | NT | PharMingen |

"+" = the antibody proved to be useful in the assay indicated;
"−" = the antibody did not work in the assay indicated;
"NT" = not tested.
*Although epitope is unknown, Thibodeau et al., Cancer Res., 56: 4836 (1996) have shown by immunohistochemical analysis that this MAb binds full-length but not mutant MLH1.

APC Immunoassay

The example shown below provides the basis of an immunoassay method to identify hereditary colon cancer of the FAP type. FAP is much less frequent than HNPCC, but provides a model system for evaluating the ability of the immunoassays of this invention to detect hereditary traits.

FAP is an autosomal-dominant inherited disease affecting about 1 in 5000 individuals in the United States (i.e., about 50,000). It is characterized by the development of hundreds to thousands of adenomatous polyps in the colon and rectum [Boman, B. M and Levin, B., "Familial polyposis," Hosp. Prac., 21: 155-170 (1986)]. These polyps can eventually progress to cancers if prophylactic colectomy is not performed [Lynch et al. H. T., Boman, B. M., Fitzgibbons, R. J., "Familial polyposis coli: genetics, surveillance and treatment," Nebr. Med. J., 73: 329-334 (1988)]. Indeed, untreated FAP patients have nearly a 100% likelihood for development of colonic cancer during their lifetime.

Germline mutations of the adenomatous polyposis coli (APC) gene occur in familial adenomatous polyposis (FAP). APC mutations are responsible for hereditary colon cancer in FAP patients, and appear to be a critical initiating factor in the development of sporadic colorectal cancer as well. Immunoassays of this invention could be useful in diagnosing individuals with previously unknown APC mutations in FAP probands, isolated cases and kindreds not yet studied because it circumvents the drawbacks of other molecular genetic methods. Diagnosing patients that carry germline APC mutations, including FAP, will lead to effective life-saving cancer prevention measures.

Most germline APC mutations (>90%) create new stop codons and other genetic changes that cause termination of translation, a mechanism which will produce a truncated APC protein with variably-sized deletions of its carboxyl portion [Miyoshi et al., "Germline mutations of the APC gene in 53 familial adenomatous polyposis patients," Proc. Natl. Acad. Sci. (USA) 89: 4452-4456 (1992); Spirio et al., Cell, 75: 951-957 (1993); Groden et al., Cell, 66: 589 (1991)]. While all germline mutations in FAP patients result in colon cancer, the variation in length of the truncated APC protein appears to correlate with other phenotypic manifestations in FAP patients. For example, germline mutations occurring in the region between codons 1250 and 1464 are associated with the clinical finding of profuse polyps (greater than ten per $cm^2$), whereas mutations occurring outside this region are associated with the observation of sparse polyps (less than ten per $cm^2$) [Nagase et al., Cancer Res., 52: 4055 (1992)]. In addition, the ocular fundus lesions associated with FAP are almost always absent if the mutation occurs 5' to exon 9 [Olschwang et al., Cell, 75: 959 (1993)]. Finally, APC mutations that occur before the fifth exon lead to both milder forms of polyposis and later onset of tumor formation. Further insight into the mechanism whereby APC mutation causes cytological changes and phenotypic differences will require determination of the actual role APC plays in colonic epithelial cells and other cell types.

Because most mutations of the APC gene in FAP create new stop codons which lead to truncated APC proteins in cells, it was hypothesized that the amount of expressed full-length APC protein is decreased. Thus the approach to detect an APC mutation is based on a simple immunoassay which detects a 50% reduced level of full-length gene product. Therefore, in cells that possess different alleles at the APC locus, involving a mutant allele along with a wild-type one, the hypothesis predicted that such heterozygotes would have only 50% of the level of full-length APC protein.

In order to test this hypothesis, cells from FAP patients were used as a "model" system in conjunction with anti-APC antibody [Boman et al., Biochem. Biophys. Res. Commun., 206: 909 (1995); Chop et al., Anticancer Res., 15: 991 (1995)] using quantitative immunoprecipitation analysis. Example 1 below verifies that hypothesis and provides evidence that it is feasible to develop a clinically useful assay to diagnose individuals that carry APC mutations in their germline.

The immunoassay methods of this invention detect the level of full-length APC protein. Others have taken the approach of identifying truncated APC proteins as determined by their migrating to a lower molecular weight position on Western blots [Smith, et al., "The APC gene product in normal and tumor cells," Proc. Natl. Acad. Sci., 90: 2846-2850 (1993)]. Although the molecular weight of the truncated APC protein provides information that is useful in localizing the mutation site, many shortened APC proteins are unstable precluding their detection on Western blots [Id.]. For example, Western blot analysis could not detect lower molecular weight bands corresponding to truncated APC proteins in three of seven FAP lymphoblastoid cell lines previously identified as containing APC mutations that lead to protein truncation [Id.]. The assays of this invention do not detect truncated APC protein, but rather the presence and quantity of the remaining full-length APC protein.

One might ask how immunoassay compares to other molecular genetic tests for detection of germline mutations. In FAP kindreds in which APC mutations have already been characterized, these mutations can be readily detected and identified in affected members simply and accurately using molecular genetic methods that directly test for the relevant mutation. Hence, using molecular genetic tests, at-risk members in such families can be accurately diagnosed as having or not having the germline APC mutation. Nonetheless, since immunoassay is so practical, it may be useful as a complementary test in diagnosing affected members of known FAP kindreds in which the APC mutation has already been identified.

In contrast, unknown APC mutations are much more difficult to detect in FAP probands, isolated cases and kindreds not yet studied because the various germline APC mutations, which mainly involve single base pair changes, small insertions, and small deletions, are known to be distributed over a large portion of the APC gene [Miyoshi et al., supra]. Also, the large size of the APC coding region (8535 base pairs) makes identification of mutations by gene sequencing very difficult, labor intensive, and costly. Therefore, other techniques have been developed and used to detect and identify the location of mutations within the APC gene.

Such techniques include denaturation gradient gel electrophoresis (DGGE), single strand conformation polymorphism (SSCP) analysis and RNAase protection analysis. The sensitivity of those techniques for detecting APC mutations in FAP patients is only 30-70% depending upon the method used, as discussed in Powell et al., "Molecular diagnosis of familial adenomatous polyposis," *N. Engl. J. Med.,* 329: 1982-1987 (1993). Newer techniques developed to detect APC mutations involving analysis of APC translation products synthesized in vitro have a slightly better sensitivity [Id.; van der Luijt et al., "Rapid detection of translation-terminating mutations at the adenomatous polyposis coli (APC) gene by direct protein truncation test," *Genomics,* 20: 1-4 (1994)]. Yet another new assay involves a rapid colorimetric method using a β-galactosidase coding sequence inserted in frame with cloned APC gene segments [Varesco et al., "A rapid screening method to detect nonsense and frameshift mutations: identification of disease-causing APC alleles," *Cancer Res.,* 53: 5581-5584 (1993)]. However, the sensitivity of this latter technique in the clinical setting has not yet been determined.

Most of the molecular genetic approaches discussed above are designed to detect single base pair changes, small insertions, and small deletions and/or mutations that lead to termination of translation. However, in some instances deletion of the entire APC gene occurs in the germline of FAP patients [Herrera et al., "Gardner Syndrome in a man with interstitial deletion of 5q," *Am. J. Med. Genetics,* 25: 473-476 (1986); Joslyn et al., "Identification of deletion mutations and three new genes at the familial polyposis locus," *Cell.* 66: 601-613 (1991); Groden et al., "Mutational Analysis of Patients with Adenomatous Polyposis: Identical Inactivating Mutations in Unrelated Individuals," *Am. J. Hum. Genet.,* 52: 263-272 (1993)], an event which would be missed by molecular genetic approaches. Moreover, some FAP patients have promoter or splicing mutations that lead to reduced levels of normal APC transcripts [Powell et al. (1993), supra]. Therefore, one recent molecular genetic approach has combined molecular detection of APC truncation-causing mutations by analysis of APC translation products synthesized in vitro with an allele-specific expression assay, which together have an improved sensitivity of 89% in detecting germline APC mutations [Powell et al. (1993), supra].

The predicted sensitivity of the immunoassays of this invention based on the ability to determine the level of full-length gene product, e.g., APC, will be close to 100% in detecting the presence of germline mutations, e.g., APC germline mutations. This approach should be valuable in detecting mutations that involve protein truncation as well as loss of allelic expression.

Overall, immunoprecipitation analysis for determining the quantity of full-length APC protein in cells should have particular usefulness in the detection of germline APC mutations that exist in the heterozygous state in FAP patients. Although other molecular tests are available, the immunoassays of this invention may have several advantages because they are relatively simple, reliable and inexpensive, and because detecting full-length gene product circumvents many drawbacks of other assays. The immunoassays should be relatively easy to perform in most hospitals or pathology laboratories. Moreover, numerous anti-APC antibodies other than APC-1 an APC-2 are available. Because the predicted sensitivity of the immunoassays of this invention is very high, the assays should also be useful in augmenting other methods based on molecular genetics where the objective is to detect previously characterized APC mutations in given FAP-kindreds so that affected members in such families can be evaluated.

Moreover, the immunoassays for full-length APC protein may be particularly useful in detecting previously unknown APC mutations in FAP probands, isolated cases and kindreds not yet studied, individuals who are otherwise difficult to diagnose. The ultimate value of the present findings for FAP patients will be realized if immunoassay of full-length APC levels finds a useful role in the clinical setting. If so, prophylactic measures (e.g. colectomy) can be instituted to prevent the development of colorectal cancer in those individuals who are identified as carrying a deleterious mutant APC allele in their germlines [Boman and Levin, "Familial polyposis," *Hosp. Pract.,* 21: 155-170 (1986); and Lynch et al. "Familial polyposis coli: genetics, surveillance and treatment," *Nebr. Med. J.,* 73: 329-334 (1988)].

Technology to Assay Protein Levels in PBLs

Purification of Lymphocytes from a Small Sample of Human Blood (20 mL.)

A commercially available method to isolate lymphocytes is that of the VACUTAINER® CPT™ Mononuclear Cell Preparation Tube (Beckton Dickinson; Franklin Lakes, N.J.). The blood is drawn into a VACUTAINER® tube which itself is spun. A gel barrier in the tube separates spun RBCs and neutrophils on the bottom from lymphocytes and monocytes on the top.

Protein Extraction

Methods of extracting protein from the purified lymphocytes were designed to be quantitative and reproducible, resulting in protein that can be assayed by immunologic techniques. An exemplary protein extraction method follows. Samples are washed 1-2 times with 5 mL of phosphate-buffered saline (PBS), and spun at 2000 rpm for 10 min at 4° C. To lyse the cells, 1× strength SDS gel loading buffer (50 mM Tris-Cl [pH 6.8], 100 mM dithiothreitol [DTT; made fresh], 2% SDS, 0.1% bromophenol blue, 10% glycerol) is added to each washed pellet (1 mL for cultured colon carcinoma cells, 200 uL for lymphocytes & lymphoblastoid cells). Cells are thoroughly mixed (vortex) and placed in boiling water (10 min). Cells are then spun for 10 min in a microfuge (Beckman Instruments Inc.; Fullerton, Calif.) to precipitate insoluble material which is discarded.

Immunoassays for Other Full-Length Proteins

The immunoassay methods of this invention can be applied to measure full-length (wild-type) proteins associated with many other hereditary and genetic disorders (cancer and non-cancer) that are due to mutations that cause protein truncation (germline and acquired) or cause the absence of allelic protein expression. Exemplary are the following genes which undergo mutations that result in truncated proteins or allelic loss.

Assays of this invention to detect and quantitate wild-type target proteins can be developed using commercially available antibodies, if such antibodies to a target protein are available. If there are no such antibodies to a target protein commercially available, or if commercially available antibodies to a target protein are found not to be suitable, suitable antibodies to a target protein can be prepared by conventional methods. [See, below under the heading "Antibodies."] A preferred representative immunoassay format of this invention is a sandwich-type, bead bound immunoassay.

1. Mutations in the BRCA1 gene are responsible for some hereditary forms of breast cancer [Hogervorst F B L, Cornelis R S, Bout M, van Vliet M, Oosterwijk J C, Olmer Renske et al., "Rapid detection of BRCA1 mutations by the protein truncation test," *Nature Genetics* 10: 208-212 (1995); Genbank Database, http://www.ncbi.nlm.nih.gov/indcgi-bin/birx_doc?genbank.]. The mRNA is 5711 base pairs in length and is located on chromosome 17q21. The percentage of cases having protein truncation causing mutations is 90% [Hogervorst et al. (1995), supra]. Monoclonal antibodies to the BRCA1 protein are commercially available from Upstate Biotechnology Inc. [Waltham, Mass. (USA)] and from Oncogene Research Products [Cambridge, Mass. (USA)].

2. Mutations in the BRCA2 gene are responsible for some hereditary forms of breast cancer [Lancaster, J. M., Wooster, R., Mangion, J., Phelan, C. M., Cochran, C., Gumbs, C. et al., "BRCA2 mutations in primary breast and ovarian cancers," *Nature Genetics,* 13: 238-240 (1996); Genbank Database, supra]. The mRNA is 10,987 base pairs in length and is located on chromosome 13q12-q13. The percentage of cases having protein truncation causing mutations is 90% [Lancaster et al., supra]. Polyclonal antibodies to the BRCA2 protein are commercially available from Lab Vision Corp. [Fremont, Calif. (USA)], from Oncogene Research Products [Cambridge, Mass. (USA)] and from Santa Cruz Biotechnology [Santa Cruz, Calif. (USA)].

3. Mutations in the ATM gene are responsible for ataxia-telangiectasia [Fitzgerald, M. G., Bean, J. M., Hegde, S. R., Unsal, H., MacDonald, D. J., Harkin, D. P. et al., "Heterozygous ATM mutations do not contribute to early onset of breast cancer," *Nature Genetics,* 15: 307-310 (1997); Genbank Database, supra]. The mRNA is 9385 base pairs in length and is located on chromosome 11q22-23. The percentage of cases having protein truncation causing mutations is 90% [Fitzgerald et al., supra]. Antibodies to the ATM protein are commercially available from Serotec Ltd. [Kidlington, Oxford (UK)].

4. Mutations in the CFTR gene are responsible for cystic fibrosis [Romey et al., "Transcript analysis of CFTR frameshift mutations in lymphocytes using the reverse transcription-polymerase chain reaction technique and the protein truncation test," *Hum. Genet.,* 98: 328-332 (1996); Genbank Database, supra]. The mRNA is 6129 base pairs in length and is located on chromosome 7q31.3. The percentage of cases having protein truncation causing mutations is 15% [Romey et al., supra]. Commercially available antibodies to the CFTR protein are not listed in Linscott's Index.

5. Mutations in the DMD gene are responsible for Duchenne muscular dystrophy [Roest et al., "Protein truncation test (PTT) for rapid detection of translation-terminating mutations," *Hum. Mol. Genet.,* 2: 1719-1721 (1993); Gardner et al., "The identification of point mutations in Duchenne Muscular Dystrophy patients by using reverse-transcription PCR and the protein truncation test," *Am. J. Hum. Genet.,* 57: 311 (1995); Genbank Database, supra]. The mRNA is 2110 base pairs in length and is located on chromosome xp21.3-p21.1. The percentage of cases having protein truncation causing mutations is 95% [Roest et al., supra; Gardner et al., supra]. Antibodies to the carboxy-terminal portion of the DMD protein are commercially available from Biomedia Corp. [Foster City, Calif. (USA)], from Biogenesis Ltd. [Sandown, N.H. (USA)], and from Biogenix Labs [San Ramon, Calif. (USA)]. Antibodies to the N-terminal portion of the DMD protein are also commercially available from those companies.

6. Mutations in the EMD gene are responsible for Emery-Dreifuss Muscular Dystrophy [Leiden, unpublished as cited in Hogervorst, F. B. L., "The Protein Truncation Test," *Promega Notes Magazine,* 62: 7-14 (1997)]. The mRNA is 503 base pairs in length and is located on chromosome Xq28. The percentage of cases having protein truncation causing mutations is 80% [Leiden, supra]. Antibodies to the EMD protein are not listed in Linscott's Index as being commercially available.

7. Mutations in the FAA gene are responsible for Fanconi anaemia [Lo Ten Foe et al., "Expression cloning of a cDNA for the major Fanconi anaemia gene, FAA," *Nat. Genet.,* 14: 320-323 (1996); Genbank Database, supra]. The mRNA is 5503 base pairs in length and is located on chromosome 16q24.3. The percentage of cases having protein truncation causing mutations is 80% [Lo Ten Foe et al., supra]. Antibodies to the FAA protein are not listed in Linscott's Index as being commercially available.

8. Mutations in the IDS gene are responsible for Hunter syndrome [Hogervorst et al., *Am. J. Hum. Genet.,* 55: A223 (1994); Genbank Database, supra]. The mRNA is 36845 base pairs in length and is located on chromosome xq27.3-q28. The percentage of cases having protein truncation causing mutations is ~50% [Hogervorst et al. (1994), supra]. Antibodies to the IDS protein are not listed in Linscott's Index as being commercially available.

9. Mutations in the NF1 gene are responsible for neurofibromatosis type 1 [Heim et al., "Screening for truncated NF1 proteins," *Nat. Genet.* 8: 218-219 (1994); Genbank Database, supra]. The mRNA is 9026 base pairs in length and is located on chromosome 17q11.2. The percentage of cases having protein truncation causing mutations is 50% [Hein et al., supra]. Antibodies to the NF1 protein are not listed in Linscott's Index as being commercially available.

10. Mutations in the NF2 gene are responsible for neurofibromatosis type 2 [MacCollin et al., "Mutational analysis of patients with neurofibromatosis 2," *Am. J. Hum. Genet.* 55: 314 (1994); Genbank Database, supra]. The mRNA is 339 base pairs in length and is located on chromosome 22q11-q13.1. The percentage of cases having protein truncation causing mutations is 65% [MacCollin et al., supra]. Antibodies to the NF2 protein are commercially available from Transduction Labs [(Lexington, Ky. (USA)].

11. Mutations in the PKD1 gene are responsible for polycystic kidney disease [Ward et al., "The polycystic kidney disease 1 gene encodes a 14 kb transcript and lies within a duplicated region on chromosome 16," *Cell,* 77: 881-894 (1994); Roelfsema and Breuning (Abstract), *Am. Soc. Hum. Genet.*: A240 (1994); Genbank Database, supra]. The mRNA is 53522 base pairs in length and is located on chromosome 16p13.3. The percentage of cases having protein truncation causing mutations is 95% [Roelfsema and Breunig, supra]. Antibodies to the PKD1 protein are not listed in Linscott's Index as being commercially available.

12. Mutations in the PTCH gene are responsible for nevoid basal cell carcinoma [Johnson et al., "Human homolog of patched, a candidate gene for the basal cell nevus syndrome," *Science,* 272, 1668-1671 (1996); Genbank Database, supra]. The mRNA is 6568 base pairs in length and is located on chromosome 9q22/3. It is known that mutations in the PTCH gene can result in a truncated protein [Johnson et al., supra; Hahn et al., *Cell.* 85: 841-851 (1996); Gailani et al., *Nature Gen.,* 14: 78-81 (1996); Unden et al., *Cancer Res.,* 56: 4562-4565 (1996); and Wicking et al., *Am. J. Hum. Genet.,* 60: 21-26 (1997)]. Antibodies to the PTCH protein are not listed in Linscott's Index as being commercially available.

13. Mutations in the c-myb gene are responsible for hematologic malignancies [Badiani et al., *Genes Dev.,* 8(7): 770-782 (1994); Schaefer et al., *J. Biol. Chem.,* 271(23): 13484-13496 (1996); Genbank Database, supra]. The mRNA is 40433 base pairs in length and is located on chromosome 6q22. It is known that mutations in this gene can cause protein truncation [Tomita et al., "Truncated c-myb expression in the human leukemic cell line TK-6," *Leukemia,* 12: 1422-1499 (1998); Jiang et al., "Minimal truncation of the c-myb gene product in rapid-onset B-cell lymphoma," *J. Virol.,* 71: 6526-6533 (1997)]. Antibodies to the c-myb protein may be commercially available from Upstate Biotechnology Inc. [Waltham, Mass. (USA)].

14. Mutations in the VHL gene are responsible for von Hippel-Lindau disease [Latif et al., "Identification of the von Hippel-Lindau disease tumor suppressor gene," *Science,* 260: 1317-1320 (1993); Genbank Database, supra]. The mRNA is 14543 base pairs in length and is located on chromosome 3p25. It is known that mutations in this gene can cause protein truncation [Olschwang et al., "Germline mutation profile of the VHL gene in von Hippel Lindau disease and in sporadic hemangioblastoma," *Human Mutation.* 12: 424-430 (1998); Ye et al., "Subcellular localization of the von Hippel Lindau disease gene product is cell-cycle dependent," *International Journal of Cancer,* 78: 62-69 (1998); Maher et al., "Phenotypic expression in von Hippel Lindau disease—Correlations with germline VHL gene mutations," *Journal of Medical Genetics,* 33: 328-332 (1996); Crossey et al., "Identification of intragenic mutations in the von Hippel Lindau disease tumor suppressor gene and correlation with disease phenotype," *Human Molecular Genetics,* 3: 1303-1308 (1994); Shuin et al., "Frequent somatic mutations and loss of heterozygosity of the von Hippel Lindau tumor suppressor gene in primary human renal cell carcinomas," *Cancer Research,* 54: 2852-2855 (1994).] von Hippel-Lindau (VHL) disease is a dominantly inherited familial cancer syndrome predisposing to retinal, cerebellar and spinal hemangioblastoma, renal cell carcinoma, pheochromocytoma and pancreatic tumors [Glavac et al., "Mutations in the VHL tumor suppressor gene and associated lesions in families with von Hippel-Lindau disease from central Europe," *Hum. Genet.,* 98(3): 271-280 (1996)]. Allele losses and mutations of the VHL gene have been shown to be involved in tumor development as in sporadic renal cell carcinoma [Brauch et al., "Hippel-Landau syndrome and sporadic renal cell carcinomas," *Pathologe,* 16 (5): 321-327 (1995)], and in cerebellar hemangioblastomas [Lee et al., "Loss of heterozygosity and mutations of von Hippel-Lindau gene on sporadic cerebellar hemangioblastoma," *Proc. Annu. Meet. Am. Assoc. Cancer Res.,* 38: A3600 (1997)]. Antibodies to the protein may be commercially available from Oncogene Research Products (Cambridge, Mass.) and PharMingen [San Diego, Calif. (USA)].

15. Mutations in the E-cadherin (HSECAD) gene are responsible for breast cancer and colon cancer [Bussemakers et al., "Molecular cloning and characterization of the human E-cadherin cDNA," *Mol. Biol. Rep.,* 17: 123-128 (1993); Genbank Database, supra]. The mRNA is 248 base pairs in length and is located on chromosome 16q22.1. It is known that mutations in this gene can cause protein truncation [Guilford et al., "E-cadherin germline mutations in familial gastric cancer," *Nature,* 392: 402-405 (1998); Vos et al., "E-cadherin inactivation in lobular carcinoma in situ of the breast: an early event in tumorigenesis," *British Journal of Cancer,* 76: 1131-1133 (1997); Berx et al., "E-cadherein is inactivated in a majority of invasive human lobular breast cancers by truncation mutations throughout its extracellular domain," *Oncogene,* 13: 1919-1925 (1996); Berx et al., "E-cadherin is a tumor invasion suppressor gene mutated in human lobular breast cancers," *EMBO Journal,* 14: 6107-6115 (1995).] Antibodies to the E-cadherin protein are commercially available from ICN Biomedicals [Costa Mesa, Calif. USA)], from Biogenex Labs [San Ramon, Calif. (USA)], from Zymed Labs [South San Francisco, Calif. (USA)], from American Research Products (Belmont, Mass.), and from Immunotech SA [Marseilles, France].

16. Mutations in the p16 gene (also known as the CDKN2A tumor-suppressor gene and MTS1 gene) are responsible for familial melanoma [Hussussian et al., "Germline p16 mutations in familial melanoma," *Nature Genetics,* 8: 15 (1994); Genbank Database, supra]. The mRNA is 422 base pairs in length and is located on chromosome 9p21. It is known that mutations in this gene can cause protein truncation [Monzon et al., "CDKN2A Mutations in Multiple Primary Melanomas," *N. Engl. J. Med.,* 338(13): 879-887 (1998)]. Antibodies to the p16 protein are commercially available from Alexis Corp [San Diego, Calif. (USA)], PharMingen [San Diego, Calif. (USA)] and Oncogene Research Products [Cambridge, Mass. (USA)].

Automated Immunoassay System

The methods of this invention can be readily adapted to automated immunochemistry analyzers. To facilitate automation of the methods of this invention and to reduce the turnaround time, a capture antibody in an immunoassay of this invention may be coupled to magnetic particles.

Antibody can be coupled to such magnetic beads by using commercially available technology as M-280 sheep anti-rabbit IgG coated Dynabeads™ from Dynal, Inc. [Lake Success, N.Y. (USA)] and rabbit antibody to a target protein, or by using M-450 Tosylactivated Dynabeads from Dynal, Inc. and covalently coupling a relevant antibody thereto. Alternatively, an agent such as glutaraldehyde could be used for covalently coupling a subject antibody to a solid support, preferably magnetic beads. Representative coupling agents can include organic compounds such as thioesters, carbodiimides, succinimide esters, diisocyanates, glutaraldehydes, diazobenzenes and hexamethylene diamines.

Target wild-type gene products and reference proteins can be quantified, for example, with a quantitative magnetic bead-based, sandwich-type of immunoassay. Such an assay can be integrated into commercially available automated immunoassay systems.

A preferred automated/immunoassay system is the ACS: 180® Automated Chemiluminescence System [Bayer Corporation; Tarrytown, N.Y. and Medfield, Mass. (USA); including ACS:180 PLUS System; ACS:180 SE System; and ACS: CENTAUR® System]. The ACS:180® Automated Immunoassay System is described in Dudley, B. S., *J. Clin. Immunoassay.* 14(2): 77 (Summer 1991). The system uses chemiluminescent labels as tracers and paramagnetic particles (PMP) as solid-phase reagents. The ACS:180 system accommodates both competitive binding and sandwich-type assays, wherein each of the steps are automated. The ACS: 180 uses micron-sized paramagnetic particles that maximize the available surface area, and provide a means of rapid magnetic separation of bound tracer from unbound tracer without centrifugation. Reagents can be added simultaneously or sequentially. Other tags, such as an enzymatic tag, can be used in place of a chemiluminescent label, such as, acridinium ester. Luminescent signals would preferably be detected by a luminometer. Also preferred is the Bayer Immuno 1™ Immunoassay System.

Controls for such an automated immunoassay system would be as exemplified by those used for the Western blot analysis of MMR proteins described herein. Positive controls could be cell lines from healthy normal volunteers. Negative controls could be cell lines known to be homozygous for a mutant gene product, e.g., HCT116 cells (homozygous for mutant MLH1 protein) and LoVo cells (homozygous for mutant MSH2 protein).

An exemplary automated immunoassay format to detect and quantitate full-length gene product, such as MLH1 and/or MSH2, would comprise: (1) a first primary antibody which is specific to the gene product, for example, specific to the amino end of said gene product, coupled to magnetic beads; (2) incubating cell lysates with said magnetic beads coated with said first primary antibody; (3) washing to reduce non-specific binding; (4) incubating with a second primary antibody specific to the carboxyl end of the full-length gene product, and which is directly labeled, preferably chemiluminescently labeled; and (5) detecting and quantitating signal from said label wherein the signal level is proportional to the amount of gene product in said cell lysate. A reporter system that is yoked to an antibody specific to the carboxyl end of the gene product is preferred as it is the full-length protein that is to be quantitated.

Various modifications to said basic automated immunoassay format can be easily envisioned by ones of skill in the art. For example, such an assay format could be varied such that two gene products, e.g. MLH1 and MSH2, or a gene product and a reference protein, e.g. APC and tubulin, β-actin or GAPH, could be detected and quantitated in the same cell lysate sample, preferably simultaneously. In the exemplary format outlined, two sets of antibodies are used wherein each set comprises two primary antibodies each of which recognizes a different epitope on the target protein.

Representative MSH2/MLH1 Automated Immunoassay

For detection and quantitation of full-length MSH2 protein, a mouse anti-MSH2 MAb, e.g., against the amino end of MSH2, could be covalently coupled to beads, such as Dynabeads® (M-450 Tosylactivated; Dynal Inc.). The beads coupled to said monoclonal antibody are incubated with cell lysates followed by a wash step. Then said washed beads are incubated with a mouse anti-MSH2, AB1, for example, a mouse MAb against the carboxyl end of MSH2, as a second primary antibody.

Analogously, an anti-MLH1 antibody, such as, a rabbit polyclonal against MLH1 (e.g., AB2 from Oncogene Research Products) could be coupled to M-280 sheep anti-rabbit IgG coated Dynabeads®. The second primary antibody could be a mouse anti-MLH1 MAb [e.g., Clone G168-728; PharMingen, (San Diego, Calif.)] which binds to the full-length but not mutant MLH1 [Thibodeau et al., Cancer Res., 56: 4836 (1996)].

The outcome of the MLH1/MSH2 assay would be acquisition of the ratio of MLH1 to MSH2 full-length protein levels, or the ratio of either wild-type protein level to a reference protein, in a single sample, preferably a cell lysate sample, more preferably a lysate from PBLs of a subject with colonic tumors (adenomas, cancers), or from a family member of a subject with colonic tumors, and of a control subject. Abnormal MLH1/MSH2 ratios would reflect a mutation or mutations in the gene which is shown thereby to express a reduced amount of wild-type, full-length gene product.

Antibodies

The term "antibodies" is defined herein to include not only whole antibodies but also biologically active fragments of antibodies, preferably fragments containing the antigen binding regions. Further included in the definition of antibodies are bispecific antibodies.

Antibodies of the invention may be prepared by conventional methods and/or by genetic engineering. Antibody fragments may be genetically engineered, preferably from the variable regions of the light and/or heavy chains ($V_H$ and $V_L$), including the hypervariable regions, and still more preferably from both the $V_H$ and $V_L$ regions. For example, the term "antibodies" as used herein includes polyclonal and monoclonal antibodies and biologically active fragments thereof including among other possibilities "univalent" antibodies [Glennie et al., Nature, 295: 712 (1982)]; Fab proteins including Fab' and F(ab')$_2$ fragments whether covalently or non-covalently aggregated; light or heavy chains alone, preferably variable heavy and light chain regions ($V_H$ and $V_L$ regions), and more preferably including the hypervariable regions [otherwise known as the complementarity determining regions (CDRs) of said $V_H$ and $V_L$ regions]; $F_c$ proteins; "hybrid" antibodies capable of binding more than one antigen; constant-variable region chimeras; "composite" immunoglobulins with heavy and light chains of different origins; "altered" antibodies with improved specificity and other characteristics as prepared by standard recombinant techniques and also by oligonucleotide-directed mutagenesis techniques [Dalbadie-McFarland et al., PNAS (USA), 79: 6409 (1982)].

Bispecific antibodies can be produced by chemically coupling two antibodies of the desired specificities. Bispecific MAbs can preferably be developed by somatic hybridization of 2 hybridomas. Bispecific MAbs for targeting two target proteins can be produced by fusing a hybridoma that produces one target specific MAb with a hybridoma producing MAbs specific to another target protein. The resulting quadromas can be screened to select a quadroma that produces a hybrid antibody having the specificity of the parent MAbs.

There are conventional techniques for making polyclonal and monoclonal antibodies that are well-known in the immunoassay art. [E.g., Galfre and Milstein, "Preparation of Monoclonal Antibodies: Strategies and Procedures," in Methods in Enzymology: Immunochemical Techniques, 73: 1-46 (Langone and Vanatis (eds); Academic Press; 1981); and in the classic reference, Kohler and Milstein, Nature, 256: 495-497 (1975).] Monoclonal antibodies specific for this invention can be prepared by immunizing appropriate mammals, preferably rodents, more preferably rabbits, rats, or mice, with an appropriate immunogen, attached to a carrier protein if necessary. Particularly preferred antibodies useful in the assays of this invention are murine monoclonal antibodies directed to epitopes on either the amino end or the carboxyl end of a subject wild-type proteins.

Representative hybridomas of this invention can be formed by the fusion of murine cell lines, human/human hybridomas [Olsson et al., PNAS (USA), 77: 5429 (1980)] and human/murine hybridomas [Schlom et al., PNAS (USA), 77: 6841 (1980); Shearman et al. J. Immunol., 146: 928-935 (1991); and Gorman et al., PNAS (USA), 88: 4181-4185 (1991)] can also be prepared among other possibilities.

Anti-peptide antibodies are also made by conventional methods in the art as described in European Patent Publication No. 44,710 (published Jan. 27, 1982). Briefly, such anti-peptide antibodies are prepared by selecting a peptide from a target amino acid sequence, chemically synthesizing it, conjugating it to an appropriate immunogenic protein and injecting it into an appropriate animal, usually a rabbit or a mouse; then, either polyclonal or monoclonal antibodies are made, the latter by a Kohler-Milstein procedure, for example.

Besides conventional hybridoma technology, newer technologies can be used to produce antibodies according to this invention. For example, the use of the PCR to clone and express antibody V-genes and the use of phage display technology to select antibody genes that encode fragments with binding activities has resulted in the isolation of antibody fragments from repertoires of PCR amplified V-genes using immunized mice or humans. [Marks et al., BioTechnology, 10: 779 (July 1992) for references; Chiang et al., BioTechniques, 7(4): 360 (1989); Ward et al., Nature, 341: 544 (Oct. 12, 1989); Marks et al., J. Mol. Biol., 222: 581 (1991); Clackson et al., Nature, 352: (15 Aug. 1991); and Mullinax et al., PNAS (USA), 87: 8095 (October 1990).

Descriptions of methods for preparing antibodies, which term is herein defined to include biologically active antibody fragments, by recombinant techniques can be found in U.S. Pat. No. 4,816,567 (issued Mar. 28, 1989); European Patent Application Publication Number (EP) 338,745 (published Oct. 25, 1989); EP 368,684 (published Jun. 16, 1990); EP 239,400 (published Sep. 30, 1987); WO 90/14424 (published Nov. 29, 1990); WO 90/14430 (published May 16, 1990); Huse et al., Science, 246: 1275 (Dec. 8, 1989); Marks et al., BioTechnology, 10: 779 (July 1992); La Sastry et al., PNAS (USA), 86: 5728 (August 1989); Chiang et al., BioTechniques, 7(40): 360 (1989); Orlandi et al., PNAS (USA), 86: 3833 (May 1989); Ward et al. Nature, 341: 544 (Oct. 12, 1989); Marks et al., J. Mol. Biol., 222: 581 (1991); and Hoogenboom et al., Nucleic Acids Res., 19(15): 4133 (1991).

Solid Phase

A solid phase that can be used in the assays of this invention may be any surface commonly used in immunoassays. For example, the solid phase may be particulate; it may be the surface of beads, for example, glass or polystyrene beads; or it may be the solid wall surface of any of a variety of containers, for example, centrifuge tubes, columns, microtiter plate wells, filters, membranes and tubing, among other containers.

When particles are used as the solid phase, they will preferably be of a size in the range of from about 0.4 to 200 microns, more usually from about 0.8 to 4.0 microns. Magnetic or magnetizable particles are a preferred particulate solid phase, and microtiter plate wells are a preferred solid wall surface. Magnetic or magnetizable particles may be particularly preferred when the steps of the methods of this invention are performed in an automated immunoassay system.

Labels

As appropriate, antibodies used in the immunoassays of this invention that are used as tracers may be labeled in any manner, directly or indirectly, that results in a signal that is visible or can be rendered visible. Detectable marker substances include radionuclides, such as $^3H$, $^{125}I$, and $^{131}I$; fluorescers, such as, fluorescein isothiocyanate and other fluorochromes, phycobiliproteins, phycoerythin, rare earth chelates, Texas red, dansyl and rhodamine; colorimetric reagents (chromogens); electron-opaque materials, such as colloidal gold; bioluminescers; chemiluminescers; dyes; enzymes, such as, horseradish peroxidase, alkaline phosphatases, glucose oxidase, glucose-6-phosphate dehydrogenase, acetylcholinesterase, $\alpha$-, $\beta$-galactosidase, among others; coenzymes; enzyme substrates; enzyme cofactors; enzyme inhibitors; enzyme subunits; metal ions; free radicals; or any other immunologically active or inert substance which provides a means of detecting or measuring the presence or amount of immunocomplex formed. Exemplary of enzyme substrate combinations are horseradish peroxidase and tetramethyl benzidine (TMB), and alkaline phosphatases and paranitrophenyl phosphate (pNPP).

Preferred detection, or detection and quantitation systems according to this invention produce luminescent signals, bioluminescent (BL) or chemiluminescent (CL). In chemiluminescent (CL) or bioluminescent (BL) assays, the intensity or the total light emission is measured and related to the concentration of the unknown analyte. Light can be measured quantitatively using a luminometer (photomultiplier tube as the detector) or charge-coupled device, or qualitatively by means of photographic or X-ray film. The main advantages of using such assays is their simplicity and analytical sensitivity, enabling the detection and/or quantitation of very small amounts of analyte.

Exemplary luminescent labels are acridinium esters, acridinium sulfonyl carboxamides, luminol, umbelliferone, isoluminol derivatives, photoproteins, such as aequorin, and luciferases from fireflies, marine bacteria, *Vargulla* and *Renilla*. Luminol can be used optionally with an enhancer molecule, preferably selected from the group consisting of 4-iodophenol or 4-hydroxy-cinnamic acid. Acridinium esters are one of the preferred types of CL labels according to this invention. Typically, a CL signal is generated by treatment with an oxidant under basic conditions.

Also preferred luminescent detection systems are those wherein the signal (detectable marker) is produced by an enzymatic reaction upon a substrate. CL and BL detection schemes have been developed for assaying alkaline phosphatases (AP), glucose oxidase, glucose 6-phosphate dehydrogenase, horseradish peroxidase (HRP), and xanthine-oxidase labels, among others. AP and HRP are two preferred enzyme labels which can be quantitated by a range of CL and BL reactions. For example, AP can be used with a substrate, such as an adamantyl 1,2-dioxetane aryl phosphate substrate (e.g. AMPPD or CSPD; [Kricka, L. J., "Chemiluminescence and Bioluminescence, Analysis by," at p. 167, *Molecular Biology and Biotechnology: A Comprehensive Desk Reference* (ed. R. A. Meyers) (VCH Publishers; N.Y., N.Y.; 1995)]; preferably a disodium salt of 4-methoxy-4-(3-phosphatephenyl) spiro [1,2-dioxetane-3,2'-adamantane], with or without an enhancer molecule, preferably, 1-(trioctylphosphoniurn methyl)-4-(tributylphosphonium methyl) benzene diochloride. HRP is preferably used with substrates, such as, 2',3',6'-trifluorophenyl 3-methoxy-10-methylacridan-9-carboxylate.

CL and BL reactions can be adapted for analysis not only of enzymes, but also of other substrates, cofactors, inhibitors, metal ions and the like. For example, luminol, firefly luciferase, and marine bacterial luciferase reactions are indicator reactions for the production or consumption of peroxide, ATP, and NADPH, respectively. They can be coupled to other reactions involving oxidases, kinases, and dehydrogenases, and can be used to measure any component of the coupled reaction (enzyme, substrate, cofactor).

The detectable marker may be directly or indirectly linked to an antibody used in an assay of this invention. Exemplary of an indirect linkage of the detectable label is the use of a binding pair between an antibody and a marker or the use of a signal amplification system.

Exemplary of binding pairs that can be used to link antibodies of assays of this invention to detectable markers are biotin/avidin, streptavidin, or anti-biotin; avidin/anti-avidin; thyroxine/thyroxine-binding globulin; antigen/antibody; antibody/anti-antibody; carbohydrate/lectins; hapten/anti-hapten antibody; dyes and hydrophobic molecules/hydrophobic protein binding sites; enzyme inhibitor, coenzyme or cofactor/enzyme; polynucleic acid/homologous polynucleic acid sequence; fluorescein/anti-fluorescein; dinitrophenol/anti-dinitrophenol; vitamin B12/intrinsic factor; cortisone, cortisol/cortisol binding protein; and ligands for specific receptor protein/membrane associated specific receptor proteins. Preferred binding pairs according to this invention are biotin/avidin or streptavidin, more preferably biotin/streptavidin.

Various means for linking labels directly or indirectly to antibodies are known in the art. For example, labels may be bound either covalently or non-covalently. Exemplary antibody conjugation methods are described in: Avarmeas et al., *Scan. J. Immunol.*, 8 (Suppl. 7): 7 (1978); Bayer et al., *Meth. Enzymol.*, 62: 308 (1979); Chandler et al., *J. Immunol. Meth.*, 53: 187 (1982); Ekeke and Abuknesha, *J. Steroid Biochem.*, 11: 1579 (1979); Engvall and Perlmann, *J. Immunol.*, 109: 129 (1972); Geoghegan et al., *Immunol. Comm.*, 7: 1 (1978); and Wilson and Nakane, *Immunofluorescence and Related Techniques*, p. 215 [Elsevier/North Holland Biomedical Press; Amsterdam (1978)].

Depending upon the nature of the label, various techniques can be employed for detecting and quantitating the label. For fluorescers, a large number of fluorometers are available. For chemiluminescers, luminometers or films are available. With enzymes, a fluorescent, chemiluminescent, or colored product can be determined or measured fluorometrically, luminometrically, spectrophotometrically or visually.

Various types of chemiluminescent compounds having an acridinium, benzacridinium, or acridan type of heterocyclic ring systems are preferred labels. Acridinium and benzacridinium esters are currently the more preferred chemiluminescent compounds, with preferred acridinium esters including those compounds having heterocyclic rings or ring systems that contain the heteroatom in a positive oxidation state including such ring systems as acridinium, benz[a]acridinium, benz[b]acridinium, benz[c]acridinium, a benzimidazole cation, quinolinium, isoquinolinium, quinolizinium, a cyclic substituted quinolinium, phenanthridinium, and quinoxalinium, as are well-known in the art.

The tracer may be prepared by attaching to the selected antibody either directly or indirectly a reactive functional group present on the acridinium or benzacridinium ester, as is well known to those skilled in the art, e.g. Weeks et al., *Clinical Chemistry.* 29(8), 1474-1479, (1983). Particularly preferred compounds are acridinium and benzacridinium esters with an aryl ring leaving group and the reactive functional group present in either the para or the meta position of the aryl ring. [See, U.S. Pat. No. 4,745,181 and WO 94/21823.]

It is to be understood that various modifications to the invention will be apparent to and can readily be made by those skilled in the art, given the disclosure herein, without departing from the scope and materials of this invention. The following examples are for purposes of illustration only and are not meant to limit the invention in any way.

Example 1

(a) Immunoprecipitation of Full-Length APC Gene Product

Anti-APC antibodies were used in this study to immunoprecipate full-length APC from the lymphocytes of FAP patients, who are known to have one mutant and one remaining wild-type APC allele in their germline. This study supports the theory underlying the immunoassays of this invention in that the lymphoblastoid cells from the FAP patients were shown to have about 50% less (50.1%±5.1%) immunoprecipitatable full-length APC protein in comparison to controls lacking germline APC mutations. The results correlate with the heterozygous APC genotypic status in FAP cells.

Materials and Methods

Anti-APC Antibody. Anti-APC polyclonal rabbit antibody (APC-2), generated in the inventor's laboratory as described elsewhere [Boman et al., "Radioimmunoassay of the APC gene product using antibodies against its middle and carboxyl regions," *Biochem. Biophys. Res. Commun.*, 206: 909-915 (1995); Chop et al., "Immunodetection of the presence or absence of full-length APC gene product in human colonic tissues," *Anticancer Res.*, 15: 991-998 (1995)], were used to perform immunoprecipitation analysis. The APC-2 antibody targets a defined epitope located in the middle region of the APC protein (amino acids 1336-1350). This antibody is active against full-length APC protein but not against the truncated APC proteins (which lack APC-2 epitopes) caused by germline APC mutations in most FAP individuals.

Cell Lines. The human colon cancer cell line HCT116 known to contain full-length APC was obtained from the American Type Culture Collection [ATCC, Manassas, Va. (USA)]. HCT116 cells were grown in DMEM containing 10% fetal bovine serum [Sigma Chemical Co., St Louis, Mo. (USA)] and a humidified atmosphere of 95% air/5% $CO_2$ at 37° C. Cultures of HCT116 cells at approximately 60-80% confluence (approximately $3 \times 10^6$ cells) in 25 $cm^2$ plastic tissue culture flasks [Corning Glass, Corning, N.Y. (USA)] were washed three times with phosphate buffered saline (PBS, Sigma), mechanically scraped from the flask bottom, pelleted by centrifugation, and then lysed for immunoprecipitation.

Five lymphoblastoid cell lines were investigated including four cell lines derived from a "married in" individual. The establishment of these cell lines by Epstein-Barr virus transformation of peripheral lymphocytes into cultures is described elsewhere [Spirio et al., "Alleles of the APC gene: An attenuated form of familial polyposis," *Cell* 75: 951-957 (1993)]. Such cells were grown in suspension culture with RPMI 1640 containing 10% FBS. Lymphoblastoid suspension cultures were processed similarly to HCT116 cells except they were pelleted by centrifugation rather than scraping from the flask.

These FAP lymphoblastoid cell lines originated from affected members in three unrelated FAP families with known APC mutations [Lynch et al., "Flat adenomas in a colon-prone kindred," *J. Natl. Cancer Inst.*, 80: 278-282 (1988); Lynch et al., "Hereditary colorectal cancer," *Semin. Oncol.*, 18: 337-366 (1991)]. These families met the criteria for FAP on the basis of detailed family histories and genetic linkage studies [Lynch et al. (1991), supra; Spirio et al., "Linkage of a variant or attenuated form of adenomatous polyposis coli to the adenomatous polyposis coli (APC) locus," *Am. J. Hum. Genet.*, 51: 92-100 (1992)].

The lymphoblastoid cell lines included FAP #1 (from individual V-27 in kindred 2764), FAP #2 (from individual IV-17 in family 2764), FAP #3 (from individual IV-26 in kindred 3101), and FAP #4 (from individual V-15 in kindred 6). The APC germline mutations have been identified in these families [Spirio (1993), supra] as follows. Two unrelated families 2764 and 3101 have an identical APC mutation in exon 4 (nucleotide change: TCATTG→TCTG) that causes a truncated APC peptide of 145 amino acids. Kindred 6 involves an APC mutation in exon 3 (TAGATAGC→TAGC) resulting in a truncated APC peptide of 83 amino acids in length.

Immunoprecipitation of APC. Semi-confluent HCT116 (approximately $3 \times 10^6$ cells in 25 $cm^2$ plastic tissue culture flasks), as well as suspension-cultured lymphoblastoid cells ($10^7$ normal or FAP immortalized WBCs), were lysed with 3 mL RIPA buffer (0.1% SDS, 0.5% deoxycholate, 1% Nonidet P-40, 100 mM NaCl, 10 mM Tris [pH 7.4]) containing protease and phosphatase inhibitors (1 mM EGTA, 12 mM EDTA, 4.3 mM $Na_2MoO_4$, 1 mM $Na_3VO_4$, 50 mM phosphate [$Na^+$ salt], 0.5 mM dithiothreitol (DTT), and 0.5 mM phenylmethylsulfonyl fluoride [PMSF]). The cell lysate was vortexed, centrifuged in a microfuge (Eppendorf) at 13,000 rpm for 10 min at 4° C., and the supernatant was collected. The protein concentration in each supernatant was determined using the Bio-Rad Protein Assay Kit (Hercules, Calif.) and the protein concentration of each supernatant was then adjusted to equal 4.35 mg/ml.

To remove non-specific binding, the supernatants (200 μl aliquots) were incubated with preimmune rabbit serum (25 μl/ml) and a 50% slurry of Protein A-Sepharose CL 4B beads (15 μl/ml, Sigma) at 4° C. for 1 hr. The samples were centrifuged as above for 15 min, and the supernatant was retained for immunoprecipitation. Anti-APC sera (APC-2) were then added to the lysates. Samples were incubated overnight at 4° C. Then Protein A-Sepharose 4B CL beads (15 μl/ml of a 50% slurry) were added, and samples were incubated on a rocking platform for 1 hr at 4° C. The Protein A-Sepharose 4B CL mixture was pelleted by centrifugation as above for 3 min and washed once with RIPA lysis buffer containing 10 mM NaCl, six times with buffer containing 0.5 M NaCl, and once more with 100 mM NaCl buffer. The Protein A-Sepharose 4B CL pellet was resuspended in gel loading buffer (50 mM Tris-HCl [pH 6.8], 100 mM DTT, 2% SDS, 0.2% Bromophenol blue, 20% glycerol), boiled for 3 min, and centrifuged. The immunoprecipitated proteins contained in the supernatants were electrophoretically separated using 2.8% agarose gels.

Proteins fractionated on agarose gels were transferred by conventional vertical capillary action blotting to a nitrocellulose membrane (0.45 um, MSI) overnight. The membrane was treated with 10% non-fat dry milk (in PBS) to block non-specific attachment of antibodies to it and then incubated with polyclonal anti-APC antibodies (APC-2 at 1:7500 dilution) overnight at room temperature. Protein bands on the blot were detected using the Amplified Alkaline Phosphates Goat Anti-Rabbit Immunoblot system (Bio-Rad Laboratories) according to the manufacturer's directions. The amount of APC protein on the immunoprecipitation blot was quantitatively determined using densitometry [Speedmaster Duo-Densitometer, Electronic Systems Engineering Co., Cushing, Okla. (USA)].

Results

Immunoprecipitation analysis detected the presence of full-length APC in HCT116 cells, in lymphoblastoid cells from a healthy subject, and in the four FAP lymphoblastoid cell lines derived from affected members in 3 unrelated FAP families. That analysis shows that the HCT116 reference cell line (known to contain full-length APC protein) clearly expresses a 300 kDa band corresponding to wild-type APC protein. The analysis also reveals that, compared to the HCT116 cell line, the lymphoblastoid cells from a healthy subject have an equivalent amount of full-length APC protein, and lymphoblastoid cells from FAP subjects have less wild-type APC protein.

Table 2 shows the relative level of immunoprecipitated full-length APC in lymphoblastoid cell lines from the different subjects as determined by densitometric evaluation of immunoprecipitation blots. HCT116 cultured carcinoma cells served to define the baseline level (100%). The lymphoblastoid cells derived from the healthy individual had a relatively similar amount of wild-type APC protein (110%) compared to that of HCT116. In contrast, the FAP cell lines had APC levels that ranged from 39% to 60% of control (mean=50.5%, SEM=5.1%).

TABLE 2

Full-length APC Protein Levels in
WBCs with Germline APC Mutations

| Cell Origin | APC Level |
|---|---|
| Controls | |
| HCT116 | 100% |
| Healthy Donor | 110% |
| FAP WBCs | |
| FAP #1 | 45% |
| FAP #2 | 58% |
| FAP #3 | 60% |
| FAP #4 | 39% |

Described in this example is the first study (to the inventor's present knowledge) which shows that APC mutations lead to a decrease in the expression of full-length APC protein. This is likely to have biological relevance because the amount of full-length APC protein in colonocytes is probably a critical factor in mechanisms underlying colon tumorigenesis. For example, it was previously hypothesized [Boman, B. M., "Biomolecular genetics of cancer," In: Lynch, H., (ed.), *Genetic Epidemiology of Cancer*, pp. 343-347, Boca Raton, Fla. CRC Press (1989)] that an APC mutation involving one APC allele may render cells more susceptible to the deleterious effects on cellular growth that are induced by other acquired genetic changes or by carcinogenic substances. The present results indicate that a reduced level of full-length APC protein actually occurs as a consequence of an APC mutation involving one APC allele.

Quantitatively, the results show that the level of anti-APC antibody immunoprecipitable protein in the FAP lymphoblastoid cell lines was about 50% of normal controls. That level of immunoreactivity is consonant with the fact that FAP patients carry only one wild-type APC allele along with one mutant allele, and with the presumption that gene product expression is proportional to gene dosage.

This example using FAP cells as a model system indicates that the immunoassays of this invention are useful to detect germline mutations that reduce target full-length protein levels. This example supports such assays as a simple, reliable, low cost way to diagnose individuals carrying a deleterious, mutant allele. Immunoassays for levels of full-length APC levels should be useful as a practical diagnostic test for detecting individuals affected with FAP.

(b) Representative APC Automated Immunoassay

For detection and quantitation of full-length MSH2 protein, a mouse anti-APC MAb, e.g., AB1 against the amino end of APC (Oncogene Research Products), could be covalently coupled to beads, such as Dynabeads® (M-450 Tosylactivated; Dynal Inc.). The beads coupled to said monoclonal antibody are incubated with cell lysates followed by a wash step. Then said washed beads are incubated with a mouse anti-APC, AB2 (Oncogene Research Products) for example, a mouse MAb against the carboxyl end of APC, as a second primary antibody.

Example 2

Western Blot Immunoassay for MLH1 and MSH2 Proteins

This example describes the measurement of MLH1 and MSH2 proteins (the expression products of 2 major MMR genes) in freshly prepared lymphocytes and in immortalized lymphocytes. The assay, which includes Western blot analysis, evaluates the expression levels of both full-length proteins simultaneously in a single lymphocyte sample. Semiquantitative analysis of levels of MLH1 and MSH2 by Western blot allows easy and direct determination of full-length MLH1/full-length MSH2 protein ratios for the same sample.

Due to the variability in sample loading and to other confounding factors, the approach used determines the individual expression level of each of the two proteins, and then the ratio of one to the other is calculated. Then it is determined whether the numerical value of the ratio falls clearly in the normal range, or clearly in the range predicted if there were 50% loss of expression of one of the two proteins.

Methods

Sample Preparation

Samples were prepared from cultures of immortalized lymphocytes. Isolated peripheral lymphocytes from healthy individuals were immortalized by Epstein Barr virus transformation to produce lymphoblastoid cell lines as described in Spiro et al., *Cell* 75: 951 (1993). Immortalized lymphocytes contained in a suspension culture (15 mL) of lymphoblastoid lymphocytes (60 to $120 \times 10^6$ cells) obtained after 7 days in culture were used.

Each sample was washed 1 to 2 times with 5 mL of phosphate-buffered saline (PBS), and spun at 2000 rpm for 10 min at 4° C. To lyse the cells, 1× strength SDS gel loading buffer (50 mM Tris-Cl [pH 6.8], 100 mM dithiothreitol [DTT; made fresh], 2% SDS, 0.1% bromophenol blue, 10% glycerol) was added to each washed pellet (1 mL for cultured colon carcinoma cells & colonic epithelium, 200 uL for lymphocytes & lymphoblastoid cells). Cells were thoroughly mixed using a vortex and then placed in a boiling water bath for 10 minutes. Cells were then spun for 10 minutes in a microcentrifuge (Beckman) to precipitate insoluble material which was discarded.

Western Blots

Supernatants (20 μL of any given cell lysate) from the above cell lysis procedure were loaded into one of the wells of the prepared gel [8% SDS-PAGE prepared according to Sambrook et al. (eds.), *A Laboratory Manual:* 18.49-18.54 [Cold Spring Harbor, N.Y. (USA); 1995)]. Positive controls, negative controls and protein markers (Bio-Rad, Cat #1610309) were always included. Positive controls included normal mucosa, SW480 and DiFi cells [human rectal adenocarcinoma cell line; Novotny-Smith et al., *J. Cell Physiol.,* 157: 253-262 (1993)] that have both MLH1 and MSH2 proteins. Controls for mutant mismatch repair proteins included HCT116 cells (MSH2 positive; MLH1 negative) and LoVo cells (MLH1 positive; MSH2 negative) (ATCC CCL-229; human adenocarcinoma cell line). A negative control that was run each time was lysate buffer containing 2% fetal bovine serum (FBS; Irvine Scientific, Calif.; Cat. #3000). Gels were run (60 to 70 volts, overnight) on a BioRad Protean II Gel Electrophoresis Apparatus [Biorad; Hercules, Calif. (USA)] until the tracker dye ran out the bottom of the gel. Proteins in the gel were transferred to a nitrocellulose membrane [NF; MSI, Westboro, Mass. (USA)] using a Bio-Rad Trans-Blot Semi-Dry Apparatus (according to Bio-Rad instructions).

Western blot hybridization was then performed by prehybridizing the NF in blocking buffer (50 mL of 5% [w/v] nonfat dry milk [Carnation] in PBS) and then incubating with two primary antibodies (mouse monoclonal Anti-MSH2 [Catalog #NA27; Titer=1:500; Oncogene Research Products] and mouse monoclonal Anti-MLH1 [Catalog #13291A; Titer=1:500; PharMingen]) in 5 ml blocking buffer for 2 hr at room temperature on a rocking platform.

The filter was then washed 3 times with 200 mL of PBS and once with TTBS buffer (20 mM Tris-Cl, pH 7.5, 500 mM NaCl, 0.05% Tween-20) and then incubated with secondary antibody (Bio-Rad goat anti-mouse antibody [GAM][Catalog #1706461; Titer=1:1000]) in 5% dry milk for 1 hr at room temperature. The NF was washed 3 times with 200 mL of TTBS buffer and then incubated in Bio-Rad color-developing solution (Catalog #1706461) according to the manufacturer's protocol. Bands were quantitatively analyzed for MSH2 or MLH1 proteins using a Gateway 2000 Computer (G6-200 XL), a Hewlett Packard Scanjet 5P scanner, and UN-SCAN-IT™ scanning software [Automated Digitizing System, Silk Scientific Corp.; Orem, Utah 84059 (USA)].

Results

Detection of levels of MMR proteins in peripheral lymphocytes. The preliminary data show that MMR proteins can be detected using Western blot analysis. Using the specific antibodies available from commercial sources (Table 1), a band for full-length protein was detected for each of the two MMR gene proteins for which antibodies are available. Western blot analysis utilized hybridization with both antibodies, anti-MLH-1 and anti-MSH-2, to show simultaneously bands for each protein, 100 kDa for MSH-2 and 80 kDa for MLH-1. This allowed semi-quantitation of levels of MLH-1 and MSH-2 (using densitometric measurement on gel bands) and direct determination of the ratio of full-length MLH-1 protein to full-length MSH-2 for the same sample. As predicted, the molecular weight (MW) of the bands were, within experimental error, the same as the known MW for the protein being assayed. Moreover, when different commercial antibody preparations (Table 1) for the MSH-2 and MLH-1 protein were used, identical results (used individually or simultaneously) were obtained, virtually ruling out the possibility of a false positive due to a non-specific, cross-reacting protein.

Conclusions from preliminary data from Western blot analysis. [1] Reliable sources of antibodies to MMR proteins exist and appear to work successfully and inexpensively in the protocols used for a representative immunoassay of this invention. [2] MMR proteins are expressed in sufficient levels in human lymphocytes to be detected by immunoassay. This was based on the ability to detect a substantial signal (band on Western blot gels) for each of the MMR proteins tested and on the finding that these bands were in the correct MW range. [3] Semi-quantitation of levels of MLH-1 and MSH-2 by Western blot analysis allows easy and direct determination of full-length MLH-1/full-length MSH-2 protein ratios for the same sample.

Table 3 illustrates the predicted meaning of the results of the MLH1 and MSH2 assay of this invention wherein a "promoter mutation" is that which eliminates transcription from one allele of the MSH2 or MLH1 gene.

The studies included in Example 2 indicated that there were reduced amounts of the respective full-length MMR protein in the cell lines deficient in either MLH1 or in MSH2, cell lines which were used as negative controls [HCT116 (MSH2+; MLH1−); and LoVo (MLH1+; MSH2−)] in comparison to the cell lines that expressed a full complement of MMR proteins [DiFi and SW480] that were used as the normal controls. Levels of MMR proteins in normal PBLs were found to approximate those found in the cell lines acting as positive controls.

Example 3

Detection of Full-Length MMR Proteins in Intact Lymphocytes by Flow Cytometry

This example shows that full-length MMR proteins can be detected successfully in intact lymphocytes by flow cytometry. Full-length MMR protein levels in cells can be accurately measured by flow cytometry. It is predicted that flow cytometry will produce fully quantitative data.

Preliminary data show that flow cytometry can be used to detect the MSH-2 protein. A lymphoblastoid line was used to establish conditions for detection of intracellular MSH-2 protein using two different anti-MSH-2 antibodies. Cells were fixed and permeabilized (using a Fix & Perm™ cell permeabilization kit; Caltag Burlingame, Calif.). Cells were incubated with one of two primary antibodies. One is anti-MSH-2 AB1 (Oncogene Research Products)—that has been pre-labeled with a fluorescent probe (phycoerythrin [P9]. This antibody is specific to the amino terminus of MSH-2. The other antibody is anti-MSH-2 AB2 (Oncogene Research Product) that has been prelabeled with fluorescein isothiocyanate [FITC]). This antibody is specific to the carboxyl terminus of MSH-2. The antibody titer that gave a reasonable signal to noise ratio for each antibody was determined. The amount of antibody binding to intracellular MSH-2 was quantitated using a FACStar$^{PLUS}$ Flow Cytometer System™ (Becton Dickinson; San Jose, Calif.). The instrument setting (fluorescence channel number or photomultiplier tube volts) was adjusted to detect relative fluorescence intensity.

Results. Both antibodies (AB1-PE & AB2-FITC) reproducibly detected intracellular MSH-2 levels in a cultured

TABLE 3

PREDICTED OUTCOMES OF OUR PROPOSED ASSAY BASED ON THE NATURE OF THE GERMLINE MMR MUTATION

| | MUTATION | | | | | |
|---|---|---|---|---|---|---|
| AFFECTED PARAMETERS | MLH1 truncation causing mutation | MSH2 truncation causing mutation | MLH1 allelic loss | MSH2 allelic loss | MLH1 promoter mutation | MSH2 promoter mutation |
| MLH1 full-length protein level | 50% | 100% | 50% | 100% | 50% | 100% |
| MSH2 full-length protein level | 100% | 50% | 100% | 50% | 100% | 50% |
| MLH1 COOH-epitope/ NH2-epitope RATIO | 50% | 100% | 100% | 100% | 100% | 100% |
| MSH2 COOH-epitope/ NH2-epitope RATIO | 100% | 50% | 100% | 100% | 100% | 100% |
| MLH1/MSH2 RATIO | 50% | 200% | 50% | 200% | 50% | 200% | lymphoblastoid cell line known to have only full-length MSH-2 protein. The flow cytometric analysis using antibodies Ab1-PE (against MSH-2 amino end) and Ab2-FITC (against MSH-2 carboxyl end) showed the presence of intracellular MSH2 protein in the lymphoblastoid cell lines.

Conclusions from flow cytometry data: [1] Using flow cytometric assays, MSH-2 protein can be qualitatively detected in an immortalized lymphocyte cell line. [2] The flow cytometric detection of full-length MSH-2 protein is almost certainly specific since detectable signals using two different anti-MSH-2 antibodies—AB1-PE and AB2-FITC—were obtained. Indeed, nuclear staining by immunofluorescence was confirmed. [3] Moreover, the flow cytometric analysis was performed using a lymphoblastoid cell line, the type of cell line that is preferred for analysis by a preferred automated immunoassay of this invention.

Example 4

Bead Bound Sandwich Immunoassay (1) Bead Bound Sandwich Immunoassay for MMR Proteins Recent experiments have established the feasibility of a preferred automated, bead-bound, sandwich-type, assay system of this invention. Anti-MSH2 antibodies were coupled to beads using 3 different techniques: 1) Ab1 antibody (against MSH-2's amino end) were coupled to Dynal tosyl-activated magnetic beads; 2) rabbit polyclonal anti-MSH2 antibodies were coupled to strepavidin-coated beads; and 3) Ab1 were coupled to magnetic beads using glutaraldehyde for cross-linking. Reporter molecules were also conjugated with a second primary antibody (Ab2) used in the sandwich-based assay by two techniques: a) Ab2 antibodies (against MSH-2's carboxyl end) were conjugated with FITC (for fluorescence); b) these same antibodies were conjugated to acridinium esters (for chemiluminescence). Significantly, similar MMR assay results were obtained using 2 types of coated beads (tosyl-activated beads and strepavidin-coated beads), and using the sandwich-based assay with a FITC-coupled second primary antibody. For example, flow cytometry showed that lysates from DiFi cells and HCT-116 cells, each of which contain only full-length MSH2 protein, had, as predicted, a measurable signal (55% positive beads), whereas a negative control cell line (LoVo) known to have only mutant truncated MSH2 protein had, as predicted, a negligible signal.

Conclusions from magnetic bead-based immunoassays. 1) This example illustrates that bead-based sandwich assays for MSH2 using flow cytometry to detect fluorescent signals from the bead-bound assay system work and are quantitative. 2) This bead-based technology is readily adaptable to an automated sandwich-type immunoassay format.

(2) HNPCC Detection in a Clinical/Community Study

The methods of section 1, above, can be used to test cohorts of CRC patients. A reduced level of MMR proteins is predicted to occur in about 10% of CRC patients. A positive test would indicate a preliminary diagnosis of HNPCC. Subsequently, that preliminary diagnosis can be confirmed by molecular genetic tests that show a genotype consistent with expression of a truncated protein.

Also, a dual antibody assay can be used, particularly to test protein from (1) HNPCC lymphocytes using immortalized lymphocytes, for which the HNPCC genotype is known; (2) from fresh lymphocytes from members of HNPCC families; and (3) from fresh, or frozen lymphocytes from CRC patients.

(2a) Testing the Assay on HNPCC Lymphocytes 2a.i. Testing MMR Levels in Immortalized Lymphocytes when the HNPCC Genotype is Known It is possible to determine levels of full-length MMR protein using lymphocytes from HNPCC patients for whom the genotype is known as the result of molecular/genetic tests. A critical control is immortalized WBCs from family members who are negative for HNPCC on genotype testing, and who are expected to have normal (100%) levels of MMR proteins.

Testing for hMLH1 is done by a "sandwich" type of immunoassay, wherein a bead-bound type of assay is performed. Such a "sandwich" type immunoassay will increase the specificity of the immunoassay.

It is predicted that cells from HNPCC positive patients will show, within a fairly narrow range of statistical variance, a 50% decrease in levels of precisely one MMR protein. The comparison groups will be: (a) freshly isolated lymphyocytes from normal, human volunteers; and (b) WBCs from family members who are negative for HNPCC on genotype testing. Also, immortalized WBCs from normal, human volunteers will be tested to evaluate the possibility that the immortalization process itself alters levels of MMR proteins. The study will confirm that a low value, 50% reduction in the ratio of the target MMR protein to a reference protein in the MMR protein assay correlates with and is capable of predicting the HNPCC form of hereditary CRC.

2a.ii. Testin Full-Length MMR Levels in Fresh Lymphocytes from Members of HNPCC Families when HNPCC Diagnosis has Been Made Testing is to be conducted using WBC samples from those CRC patients having a positive family history for HNPCC (not immortalized; no genotype available). Use of the Amsterdam Criteria and genetic testing suggest that 70 to 80% of CRC patients in such families will have a positive genotype (from molecular genetic tests) for HNPCC (mutation in one of four mismatch repair genes).

It is predicted that: (a) among members of HNPCC families, who are at 50% risk of having inherited a mutant MMR gene (because this is an autosomal dominant gene), 50% will show significantly reduced levels of an MMR protein; (b) there will be about a 50% reduction in the levels of one MMR protein that is expressed by the cell containing the mutant gene (due to loss of one of the two wild-type alleles); (c) molecular genetic tests can be used to confirm both positive and negative diagnoses of HNPCC determined by the immunoassays of this invention. The testing described in this subsection should confirm the predictive value of the assays of this invention for diagnosing HNPCC among members of HNPCC families under field conditions.

2a.iii. Testing the General Population of Patients with Colorectal Cancer (CRC)

This experiment is similar to the preceding one (2aii) except that a more diverse population of patients will be studied, namely, all of those with CRC. It is predicted that: (1) 10% of all CRC patients will prove to have HNPCC by the criterion of a positive finding in the assay (based on published studies); (2) molecular genetic tests will confirm that individuals who are positive in the assay are truly HNPCC positive.

The testing described in this subsection should confirm the predictive value of the assays of this invention for diagnosing HNPCC among members of CRC patients under field conditions. A variation of the testing will be to study patients with cancers other than CRC but known to be associated with HNPCC such as endometrial cancer. Whether a significant fraction of such patients are positive for MMR mutations will be determined.

2a.iv. Establishing a Data-Base of MMR Values in Cancer and Non-Cancer Patients

A data-base of "full-length" MMR values for both normal, human volunteers and HNPCC patients will be established so that the "normal" range for full-length MMR protein levels can be determined. Since HNPCC is currently believed to represent about 10% of all cases of CRC, and an even smaller fraction of all cancers, it is predicted that the vast majority of CRC patients and patients with other forms of cancer will have full-length MMR values in the "normal" range. This data base will eventually include results from molecular genetic tests that should confirm the accuracy of the MMR protein test in diagnosing HNPCC.

(2b) Testing a Variant Immunoassay—One that Uses Two Antibodies and a "Sandwich" Technique and that is Adaptable to Automation In this assay, an antibody that recognizes one of the MMR proteins is immobilized (e.g., in the wells of a 96-well microtitre plate). A lysate of a sample of peripheral lymphocytes from a patient is added to allow the particular MMR protein to bind to the plate. The lysate is removed by washing and a second antibody is added that recognizes a different epitope on the MMR protein and that incorporates a reporter molecule for quantitation of the amount of full-length protein in the sample. The sandwich assay will be adapted to an automated ELISA-based system.

The description of the foregoing embodiments of the invention have been presented for purposes of illustration and description. They are not intended to be exhaustive or to limit the invention to the precise form disclosed, and obviously many modifications and variations are possible in light of the above teachings. The embodiments were chosen and described in order to explain the principles of the invention and its practical application to enable thereby others skilled in the art to utilize the invention in various embodiments and with various modifications as are suited to the particular use contemplated.

All references cited herein are hereby incorporated by reference.

The invention claimed is:

1. A method of screening for hereditary breast cancer or a predisposition to hereditary breast cancer in an organism, said screening method comprising:
   (a) isolating a biological sample containing normal cells from said organism;
   (b) immunologically quantitating the levels of full-length BRCA1 and full-length BRCA2 in said normal cells;
   (c) calculating the ratio of the level of full-length BRCA1 in said normal cells, to the level of full-length BRCA2 in said normal cells; and
   (d) determining whether the ratio calculated in step (c) reflects about a 50% decrease from a normal level of BRCA1 or BRCA2, wherein said normal level of BRCA1 or BRCA2 is determined in individuals unaffected by said hereditary breast cancer or predisposition to hereditary breast cancer;
   (e) whereby if the ratio calculated in step (c) indicates that there is about a 50% decrease from said normal level of either full-length BRCA1 or full-length BRCA2 in said normal cells, that the subject organism has hereditary breast cancer or has a predisposition to hereditary breast cancer.

2. The method of claim 1 wherein step (d) comprises comparing the ratio calculated in step (c) to the mean of ratios calculated from the levels of full-length BRCA1 and full-length BRCA2 proteins in comparable biological samples from organisms of the same taxonomic classification as the subject organism, wherein said organisms of the same taxonomic classification as the subject organism are unaffected by said hereditary breast cancer or predisposition to hereditary breast cancer.

3. The method of claim 1 wherein said organism is a vertebrate.

4. The method of claim 3 wherein said vertebrate is a mammal.

5. The method of claim 4 wherein said mammal is a human.

6. The method of claim 1 wherein said about 50% decrease from the normal level of full-length BRCA1 or full-length BRCA2 is the result of a mutation selected from the group consisting of truncating-causing mutations and mutations that cause allelic loss.

7. The method of claim 1 wherein said about 50% decrease from the normal level of full-length BRCA1 or full-length BRCA2 is the result of a mutation selected from the group consisting of nonsense mutations, frameshift mutations, promoter mutations, enhancer mutations, splice site mutations, null mutations, and poly-A tail mutations.

8. The method of claim 1 wherein said biological sample is selected from the group consisting of body fluids containing cells and tissue specimens.

9. The method of claim 8 wherein said body fluids are selected from the group consisting of blood, serum, plasma, semen, breast exudate, gastric secretions, fecal suspensions, bile, saliva, tears, sputum, mucous, urine, lymph, cytosols, ascites, pleural effusions, amniotic fluid, bladder washes, bronchoalveolar lavages, and cerebrospinal fluid.

10. The method of claim 1 wherein said normal cells are peripheral blood lymphocytes.

11. The method of claim 1 wherein said method is diagnostic for hereditary breast cancer or a predisposition to hereditary breast cancer, or is diagnostic/prognostic for hereditary breast cancer.

12. The method of claim 1 wherein the levels of full-length BRCA1 and full-length BRCA2 are determined by Western blot analysis, by immunoprecipitation and then by Western blot analysis, by flow cytometry, by EIA, by ELISA, by RIA, by competition immunoassay, by dual antibody sandwich assay, by chemiluminescent assay, by bioluminescent assay, by fluorescent assay, or by agglutination assay.

13. The method of claim 1 which is automated.

* * * * *